US008765973B2

(12) United States Patent
Raines et al.

(10) Patent No.: US 8,765,973 B2
(45) Date of Patent: Jul. 1, 2014

(54) ETOMIDATE ANALOGUES THAT DO NOT INHIBIT ADRENOCORTICAL STEROID SYNTHESIS

(75) Inventors: Douglas E. Raines, Wayland, MA (US); Joseph F. Cotten, Grafton, MA (US); Stuart A. Forman, Arlington, MA (US); Keith W. Miller, Lincoln, MA (US); Syed S. Husain, Newton, MA (US); Gregory D. Cuny, Houston, TX (US)

(73) Assignee: The General Hospital Corporation, Boston, MA (US)

(*) Notice: Subject to any disclaimer, the term of this patent is extended or adjusted under 35 U.S.C. 154(b) by 110 days.

(21) Appl. No.: 13/382,544

(22) PCT Filed: Jul. 8, 2010

(86) PCT No.: PCT/US2010/041379
§ 371 (c)(1),
(2), (4) Date: Jul. 7, 2012

(87) PCT Pub. No.: WO2011/005969
PCT Pub. Date: Jan. 13, 2011

(65) Prior Publication Data
US 2013/0079381 A1     Mar. 28, 2013

Related U.S. Application Data

(60) Provisional application No. 61/224,751, filed on Jul. 10, 2009.

(51) Int. Cl.
C07D 207/337    (2006.01)
A61K 31/40      (2006.01)

(52) U.S. Cl.
USPC ............................................ 548/532; 514/423

(58) Field of Classification Search
CPC .......................... C07D 207/337; A62K 31/40
USPC ........................................... 548/532; 514/423
See application file for complete search history.

(56) References Cited

U.S. PATENT DOCUMENTS

| 3,354,173 | A | 11/1967 | Godefroi et al. |
| 4,038,286 | A | 7/1977 | Roevens et al. |
| 4,289,783 | A | 9/1981 | Mesens |
| 5,019,583 | A | 5/1991 | Feldman et al. |
| 5,041,554 | A | 8/1991 | Parker et al. |
| 5,242,939 | A | 9/1993 | Sircar |
| 5,283,341 | A | 2/1994 | Tanaka et al. |
| 5,466,700 | A | 11/1995 | Batenhorst et al. |
| 8,557,856 | B2 * | 10/2013 | Raines et al. ............... 514/400 |
| 2003/0055023 | A1 | 3/2003 | Rajewski et al. |
| 2003/0181481 | A1 | 9/2003 | Carson et al. |

FOREIGN PATENT DOCUMENTS

| EP | 0289066 | 11/1988 |
| EP | 0381141 A2 | 8/1990 |
| JP | 06345728 | 12/1994 |
| WO | 9639137 | 12/1996 |
| WO | 2006023844 A2 | 3/2006 |

OTHER PUBLICATIONS

Atucha et al. (Bioorg. Med. Chem. Lett., 19 (2009) 4284-4287).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chapters 9-10 provided.*
David et al. (J. Org. Chem, vol. 69, No. 8, 2004, p. 2888-2891).*
Earle, M. J., et al., "Alkylation Reactions of N-Alkylpyrroles Resulting in the Diastereoselective Formation of Diarylacetic Esters" Synlett, 1992, No. 9, pp. 745-747.
Cui et al., Angew. Chem. Int. Ed., 48:5737-5740 (2009). "Chemoselective Asymmetric N-Allylic Alkylation of Indoles with Morita-Baylis-Hillman Carbonates."
David et al., J. Org. Chem., 69:288-2891 (2004). "Novel Routes to Chiral 2-Alkoxy-5-/6-methoxycarbonylmethylidenepyrrolidines/-piperidines."
Davies et al., Synlett, 7:1146-1148 (2002). "Ring Closing Metathesis for the Asymmetric Synthesis of (S)-Homopipecolic Acid, (S)-Homoproline and (S)-Coniine."
Ferris et al., Tetrahedron Letters, 37(1):107-110 (1996). "New Chiral Rhodium (II) Carboxylates and their Use as Catalysts in Carbenoid Transformations."
Sircar et al, J. Med. Chem., 36:1735-1745 (1993). "Nonpeptide Angiotensin II Receptor Antagonists. 1. Synthesis and in Vitro Structure-Activity Relationships of [[[(1H-Pyrrol-1-ylacetyl)amino]phenyl]methyl]imidazole Derivatives as Angiotensin II Receptor Antagonists."
Teng et al., Bioorganic and Medicinal Chemistry Letters, 18:3219-3223 (2008). "Structure-activity relationship and liver microsome stability studies of pyrrole necroptosis inhibitors."
De Coster, et al. "Comparison of the effects of etomidate and its fluoro analogue, R 8110, on plasma cortisol, 11β-deoxycortisol, 17α-hydroxyprogesterone and testosterone concentrations in dogs," J. Vet. Pharmacol. Therap. 10:227-232 (1987).
De Coster, et al. "Comparative effects of etomidate and its fluoro analogue, R 8110 on testicular, adrenal and ovarian steroid biosynthesis," J. Vet. Pharmacol. Therap. 11:345-353 (1988).

(Continued)

Primary Examiner — Robert Havlin
(74) Attorney, Agent, or Firm — Nixon Peabody LLP

(57) ABSTRACT

The invention is directed to compounds according to formula (I): where $R_1$ is $L_1C(O)OT$ or $L_1C(O)OL_2C(O)OT$; $R_2$ is a substituted or unsubstituted $C_1$-$C_{10}$ alkyl, $C_2$-$C_{10}$ alkenyl, or $C_2$-$C_{10}$ alkynyl, or $R_1$; n is an integer from 0 to 5; each $R_3$ is independently halogen or $R_2$; $R_4$ and $R_5$ are independently H, halogen, CN or $CF_3$; $L_1$ and $L_2$ are each independently a bond, a substituted or unsubstituted $C_1$-$C_{10}$ alkylene, $C_2$-$C_{10}$ alkenylene, or $C_2$-$C_{10}$ alkynylene; and T is H, a substituted or unsubstituted $C_1$-$C_{10}$ alkyl, $C_2$-$C_{10}$ alkenyl, or $C_2$-$C_{10}$ alkynyl, nitrophenol, or cyclopropyl. The invention is also directed to a pharmaceutical composition comprising a compound according to formula (I) and a pharmaceutically acceptable carrier, and to methods for providing anesthesia in mammals by administering such a pharmaceutical composition.

16 Claims, 8 Drawing Sheets

(56) References Cited

OTHER PUBLICATIONS

Godefroi, et al. "DL-1-(1-Arylalkyl)imidazole-5-carboxylate Esters. A Novel Type of Hypnotic Agents," J. Medicinal Chemistry 8:220-223 (1964).

Van Dijk, et al. "R 8110, a new short-acting hypnotic in dogs," Research in Veterinary Science 42:200-203 (1987).

Arden et al., "Increased Sensitivity to Etomidate in the Elderly: Initial Distribution versus Altered Brain Response," Anesthesiology, 65:19-27 (1986).

De Jong et al., "Etomidate Suppresses Adrenocortical Function by Inhibition of 11β-Hydroxylation," J Clin Endocrinol Metab, 59(6):1143-7 (1984).

Hotchkiss et al., "The Pathophysiology and Treatment of Sepsis," N Engl J Med, 348(2):138-50 (2003).

Husain, et al., "2-(3-Methyl-3H-diaziren-3-yl)ethyl 1-(1-phenylethyl)-1H-imidazole-5-carboxylate: A Derivative of the Stereoselective General Anesthetic Etomidate for Photolabeling Ligand-Gated Ion Channels," J Med Chem, 46:1257-65 (2003).

Jurd, et al., "General anesthetic actions in vivo strongly attenuated by a point mutation in the GABA-A receptor β3 subunit," Faseb J, 17(2):250-2 (2002).

Lamberts, et al., "Differential Effects of the Imidazole Derivatives Etomidate, Ketoconazole and Miconazole and of Metyrapone on the Secretion of Cortisol and its Precursors by Human Adrenocortical Cells," J Pharmacol Exp Ther, 240(1):259-64 (1987).

Li, et al., "Identification of a GABAa Receptor Anesthetic Binding Site at Subunit Interfaces by Photolabeling with an Etomidate Analog," J Neurosci, 26(45):11599-11605 (2006).

Podust, et al., "Crystal structure of cytochrome P450 14α-sterol demethylase (CYP51) from *Mycobacterium tuberculosis* in complex with azole inhibitors," Proc Natl Acad Sci USA, 98(6):3068-3073 (2001).

Ray, et al., "Effect of induction agent on vasopressor and steroid use, and outcome in patients with septic shock," Crit Care, 11(3):R56 (2007).

Roumen, et al., "Construction of 3D models of the CYP11B family as a tool to predict ligand binding characteristics," J Comput Aided Mol Des, 21:455-71 (2007).

Rüsch, et al., "Gating Allosterism at a Single Class of Etomidate Sites on α1β2γ2L GABAa Receptors Accounts for both Direct Activation and Agonist Modulation," J Biol Chem, 279(20):20982-92 (2004).

Sprung, et al., "Hydrocortisone Therapy for Patients with Septic Shock," N Engl J Med, 358(2):111-24 (2008).

Stewart, et al., "Tryptophan Mutations at Azi-Etomidate Photo-Incorporation Sites on α1 or β2 Subunits Enhance GABAa Receptor Gating and Reduce Etomidate Modulation," Mol Pharmacol, 74(6):1687-95 (2008).

Verras, et al., "Cytochrome P450 active site plasticity: attenuation of imidazole binding in cytochrome P450cam by an L244A mutation," Protein Eng Des Sel, 19(11):491-6 (2006).

Watt, et al., "Mortality amongst multiple trauma patients admitted to an intensive therapy unit," Anaesthesia, 39:973-81 (1984).

Zhao, et al., "Structure of Microsomal Cytochrome P450 2B4 Complexed with the Antifungal Drug Bifonazole," J Biol Chem, 281(9):5973-81 (2006).

Xu, et al., "Catecholamine and Histidyl Protein Cross-Linked Structures in Sclerotized Insect Cuticle," Insect Biochemistry and Molecular Biology, 27(2):101-108 (1997).

Swain, et al., "Geometric Preferences of Crosslinked Protein-Derived Cofactors Reveal a High Propensity for Near-Sequence Pairs," Proteins: Structure, Function, and Bioinformatics, 59:64-71 (2005).

Chivikas, et al., "Phenacyl-Directed Alkylation of Imidazoles: A New Regiospecific Synthesis of 3-Substituted L-Histidines," Journal of Organic Chemistry, 52:3591-3594 (1987).

Jagr, et al., "Synthesis and Characterization of Styrene Oxide Adducts with Cysteine, Histidine, and Lysine in Human Globin," Chemical Research in Toxicology, 20:1442-1452 (2007).

* cited by examiner

ETOMIDATE ANALOGUES THAT DO NOT INHIBIT ADRENOCORTICAL STEROID SYNTHESIS

CROSS REFERENCE TO RELATED APPLICATIONS

This application is a 35 U.S.C. §371 National Stage Entry Application of International Application No. PCT/US2010/041379, filed Jul. 8, 2010, which designates the U.S., and which claims benefit under 35 U.S.C. §119(e) of the U.S. Provisional Application No. 61/224,751, filed Jul. 10, 2009, the content of which is incorporated herein by reference in its entirety.

GOVERNMENT SUPPORT

This invention was made with Government support under Grant No. P01-58448 awarded by the National Institutes of Health. The Government has certain rights in the invention.

FIELD OF THE INVENTION

This invention relates to etomidate analogues that have improved pharmacokinetic and pharmacodynamic properties and their use as anaesthetics.

BACKGROUND OF THE INVENTION

The incidence of sepsis is approximately 750,000 per year in the US with a mortality of 30 to 50% and an annual cost of $17 billion (Hotchkiss, R. S. and I. E. Karl, The pathophysiology and treatment of sepsis. N Engl J Med, 2003. 348(2): p. 138-50). When severe, sepsis is often associated with profound hypotension, massive vasodilation, shock, and multiple organ failure. Patients with sepsis commonly need general anesthesia for important therapeutic interventions such as intubation and surgery. Unfortunately, all general anesthetics produce serious and potentially life-threatening side effects, particularly in critically ill patients with sepsis. Of greatest concern is cardiovascular depression, which is produced by nearly all anesthetics.

Etomidate is a highly potent IV anesthetic that is distinguished from other general anesthetics by its ability to maintain cardiovascular stability. It induces loss of righting reflex in tadpoles (Husain, S. S., et al., 2-(3-Methyl-3H-diaziren-3-yl)ethyl 141-phenylethyl)-1H-imidazole-5-carboxylate: a derivative of the stereoselective general anesthetic etomidate for photolabeling ligand-gated ion channels. J Med Chem, 2003. 46(7): p. 1257-65) and loss of responsiveness in humans (Arden, J. R., F. O. Holley, and D. R. Stanski, Increased sensitivity to etomidate in the elderly: initial distribution versus altered brain response. Anesthesiology, 1986. 65(1): p. 19-27) at a concentration of ~2 µM. At the molecular level, there is compelling evidence that etomidate produces anesthesia by modulating the function of $GABA_A$ receptors (Jurd et al., Faseb J (2003) 17(2): 250-2 and Rusch et al., J Biol Chem (2004) 279(20): 20982-92). Etomidate enhances $GABA_A$ receptor-mediated currents evoked by low concentrations of GABA, but has little effect on currents evoked by high concentrations of GABA. This shifts the GABA concentration-response curve leftward, reducing the GABA EC50. This receptor mechanism is also thought to account for the anesthetic action of propofol.

There is a growing understanding of where etomidate acts on the $GABA_A$ receptor to produce anesthesia. Photoaffinity labeling studies have identified two amino acids in $GABA_A$ receptors that contribute to the etomidate binding site: Met-236 on the α subunit and Met-286 on β the subunit (Li et al., J Neurosci (2006) 26(45): 11599-605). Structural homology modeling of the $GABA_A$ receptor based on the Torpedo acetylcholine receptor structure strongly suggests that these two amino acids contribute to an anesthetic binding pocket located at the interface between α and β subunits. This conclusion is supported by mutagenesis studies showing that mutating these amino acids to a tryptophan attenuates the receptor's sensitivity to etomidate (Stewart et al., Mol Pharmacol (2008) 74(6): 1687-95).

Inhibition of steroid synthesis is a potentially deadly side effect of etomidate administration, particularly in critically ill patients, e.g., patients with sepsis, who might otherwise benefit most from its use. This inhibition is extremely potent, occurring at doses of etomidate that are below those which produce general anesthesia. It is also extremely dangerous as it significantly increases the mortality of critically ill patients who have received continuous etomidate infusions. For example, Watt, I. and I. M. Ledingham, Anaesthesia (1984) 39(10): 973-81, retrospectively found that critically ill trauma patients more commonly required vasopressors (p<0.0001) and had a mortality that was nearly 3-fold higher (77% vs. 28%; p<0.0005) when sedated with etomidate vs. benzodiazepines even after matching for age, gender, and injury severity score. Because of its effect on steroid synthesis, etomidate cannot be safely administered to critically ill patients as a prolonged continuous infusion and the administration of even a single IV bolus dose for anesthetic induction in septic patients has recently raised concerns. It has been suggested that such morbidity and mortality might be reduced by empirically administering exogenous steroids (Ray, D. C. and D. W. McKeown, Crit Care (2007) 11(3): R56); however, this approach is suboptimal as the dosing, timing, and duration of steroid therapy in any given patient would be speculative. Furthermore, the administration of exogenous steroids can itself produce significant complications (particularly in the setting of sepsis) including altered glucose homeostasis, impaired wound healing, and immunosuppression. It has been suggested that these complications explain, at least in part, the results of the CORTICUS study indicating that while exogenous steroids reduce vasopressor requirements, they don't improve survival even in critically ill patients deemed to have adrenocortical insufficiency (Sprung et al., N Engl J Med (2008) 358(2): 111-24).

Etomidate suppresses adrenocortical steroid synthesis primarily by binding to and inhibiting 11βhydroxylase (i.e. CYP11B1), a cytochrome P450 enzyme that is necessary for the biosynthesis of cortisol, corticosterone, and aldosterone (de Jong et al., J Clin Endocrinol Metab (1984) 59(6): 1143-7). Etomidate's half-maximal inhibitory concentration (IC50) is in the low nanomolar range (Lamberts et al., J Pharmacol Exp Ther (1987) 240(1): 259-64 and Roumen et al., J Comput Aided Mol Des (2007) 21(8): 455-71), a concentration range that is orders of magnitude lower than its hypnotic/anesthetizing concentration.

Previous crystallographic studies of imidazole-containing drugs (e.g. ketoconazole) to various cytochrome P450 enzymes have shown that high affinity binding requires a strong attractive interaction ("coordination") between the basic nitrogen in the drug's imidazole ring and the heme iron at the enzyme's catalytic site (Zhao et al., J Biol Chem (2006) 281(9): 5973-81; Podust et al., Proc Natl Acad Sci USA (2001) 98(6): 3068-73; and Verras et al, Protein Eng Des Sel (2006) 19(11): 491-6); cytochrome P450 enzymes (including 11β-hydroxylase) contain heme prosthetic groups at their catalytic sites. Although 11β-hydroxylase has not yet been crystallized nor its interaction with etomidate defined, homology modeling studies suggest that high affinity binding of etomidate to 11β-hydroxylase also requires coordination between the basic nitrogen in etomidate's imidazole ring and the enzyme's heme iron. This led to the prediction that high affinity binding to 11β-hydroxylase (and thus adrenolytic activity) could be "designed out" of etomidate (without disrupting potent anesthetic and $GABA_A$ receptor activities) by replacing this basic nitrogen with other chemical groups that cannot coordinate with heme iron. This would be highly desirable because it allows for potent anesthetic and $GABA_A$ receptor modulatory activities while not suppressing adrenocortical function at clinically relevant doses.

There is a great need for safer general anesthetics for use in critically ill patients, and particularly for patients with sepsis. (R)-Etomidate possesses many properties that would make it an ideal anesthetic agent (e.g. high anesthetic potency, lesser effects on cardiovascular function and higher therapeutic index than other agents) if it were not such a potent inhibitor of adrenocortical function.

Thus, there is a need in the art to develop analogues of (R)-etomidate that retain its many beneficial properties (e.g. rapid onset of action, little effect on blood pressure, high therapeutic index), but do not cause potentially dangerous inhibition of adrenocortical function. Such analogues will permit anesthesia to be administered more safely to patients who are critically ill. This invention answers that need.

SUMMARY OF THE INVENTION

The invention is directed to compounds according to formula (I):

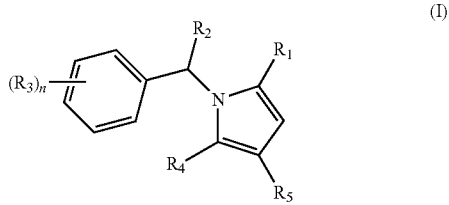

wherein,
$R_1$ is $L_1C(O)OT$ or $L_1C(O)OL_2C(O)OT$;
$R_2$ is a substituted or unsubstituted $C_1$-$C_{10}$ alkyl, $C_2$-$C_{10}$ alkenyl, or $C_2$-$C_{10}$ alkynyl, or $R_1$;
n is an integer from 0-5;
each $R_3$ is independently halogen or $R_2$;
$R_4$ and $R_5$ are independently hydrogen, halogen, CN or $CF_3$;
$L_1$ and $L_2$ are each independently a bond, a substituted or unsubstituted $C_1$-$C_{10}$ alkylene, $C_2$-$C_{10}$ alkenylene, or $C_2$-$C_{10}$ alkynylene, wherein the backbone of alkylene may contain one or more heteroatoms; and
T is H, a substituted or unsubstituted $C_1$-$C_{10}$ alkyl, $C_2$-$C_{10}$ alkenylene, $C_2$-$C_{10}$ alkynylene, nitrophenol, or cyclopropyl, wherein the backbone of alkyl may contain one or more heteroatoms.

The compounds of formula (I) include pharmaceutically acceptable salts, stereoisomer mixtures, and enantiomers thereof.

Compounds of formula (I) have improved pharmacokinetic and pharmacodynamic properties over (R)-etomidate that allow for equivalent or improved anesthetic properties along with a reduction in undesirable side effects. Compounds of formula (I) are analogues of etomidate that retain (R)-etomidate's beneficial anesthetic properties, but do not cause clinically significant inhibition of adrenocortical function.

Another aspect of the invention is directed to a pharmaceutical anesthetic composition comprising an effective amount of a compound according to formula (I) and a pharmaceutically acceptable carrier.

Yet another aspect of the invention is directed to a method for providing anesthesia in a mammal or including administering to the mammal an effective anesthetic compound of formula (I) or a pharmaceutical composition.

Another aspect of the present invention is use of the compounds of formula (I) substantially as described herein as a formulation for, or in the manufacture of a formulation for providing anesthesia in a subject in need thereof.

BRIEF DESCRIPTION OF THE DRAWINGS

In FIG. 2A, each data point represents the results from a single tadpole. In FIG. 2B, each data point represents the average of five tadpoles. The curve is fit of the data set using the method of Waud D R, J Pharmacol Exp Ther, (1972) 183(3): 577-607. A total of 40 tadpoles were used to define this concentration-response curve.

FIG. 4A are traces showing reversible enhancement by 10 μM carboetomidate of currents mediated by wild-type receptors when evoked by EC5-10 γ-aminobutyric acid. FIG. 4B are traces showing minimal enhancement by 10 μM carboetomidate of currents mediated by etomidate-insensitive mutant receptors when evoked by EC5-10 γ-aminobutyric acid.

DETAILED DESCRIPTION OF THE INVENTION

Figure 1:
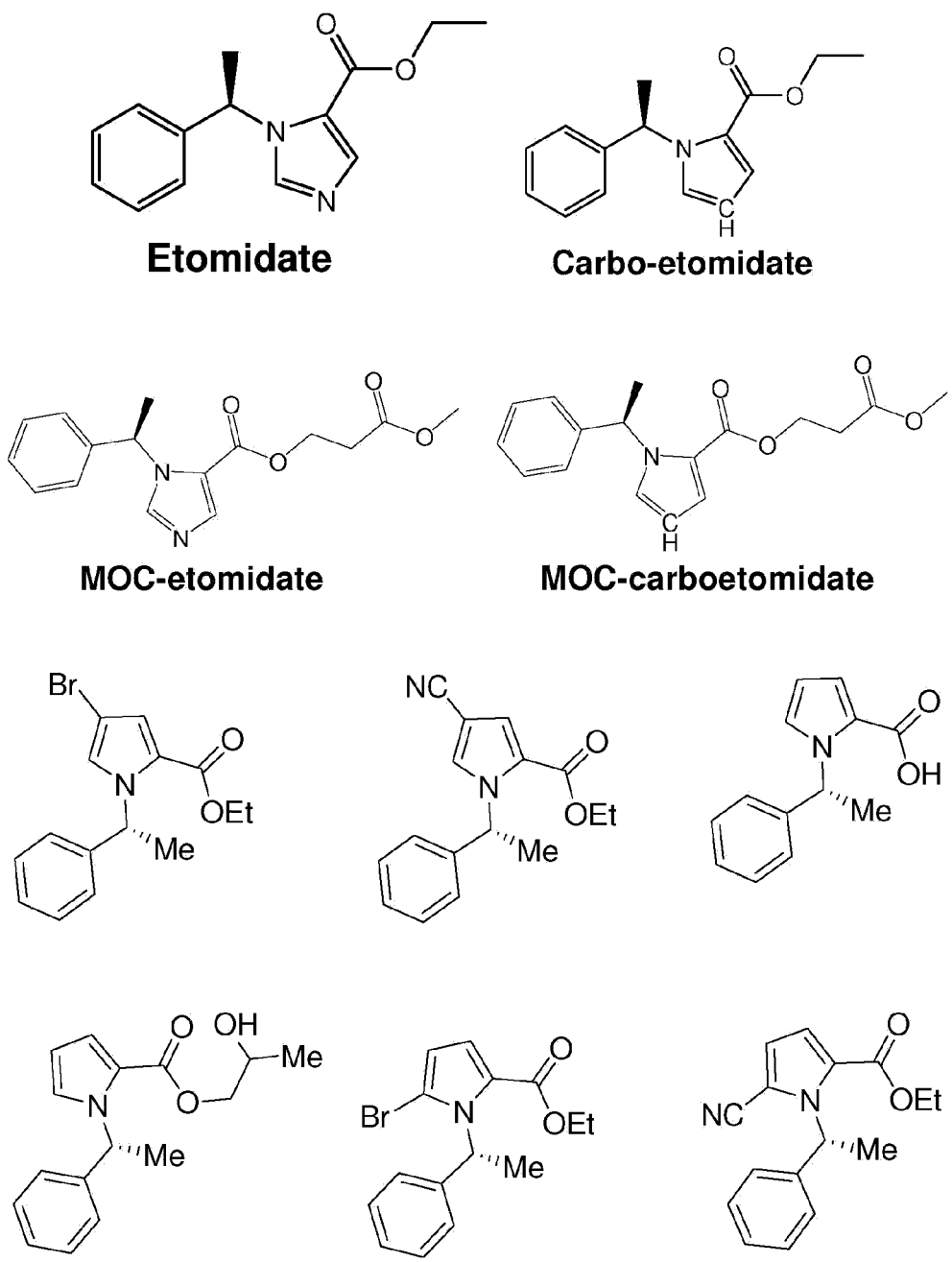
FIG. 1 shows the structures of Etomidate (ethyl 3-(1-phenylethyl)imidazole-4-carboxylate), carboetomidate (ethyl 3-(1-phenylethyl)pyrrole-2-carboxylate), MOC-etomidate, MOC-carboetomidate, and analogs of carboetomidate.

This invention relates to safer analogues of (R)-etomidate that retain its beneficial characteristics (e.g. potent anesthetic, rapid onset of anesthesia, little effect on blood pressures), but whose impact on adrenocortical steroid synthesis is substantially reduced.

The compounds of the invention can be understood as analogues of etomidate (either R- or S-enantiomer) wherein the basic nitrogen has been replaced with a CH group. Without wishing to be bound by theory, replacement of basic nitrogen with CH group reduced the binding affinity of these compounds for 11β-hydroxylase. The compounds of the invention can be further augmented with one or more additional metabolically-labile ester moieties attached to various positions of the core molecule directly or via various linker groups (for example, —$CH_2CH_2$—). Distal to the ester moieties, there may be a "tail" group (for example, —$CH_3$). The various embodiments of this invention are discussed below.

The invention is directed to compounds according to formula (I):

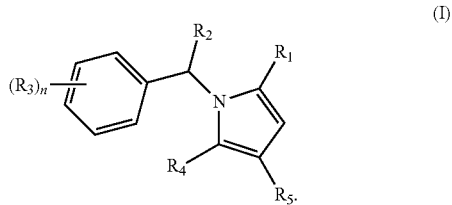

(I)

$R_1$ is $L_1C(O)OT$ or $L_1C(O)OL_2C(O)OT$. In a preferred embodiment, $R_1$ is $L_1C(O)OT$.

$R_2$ is a substituted or unsubstituted $C_1$-$C_{10}$ alkyl, $C_2$-$C_{10}$ alkenyl, or $C_2$-$C_{10}$ alkynyl, or $R_1$. Preferably, $R_2$ is an alkyl, such as $CH_3$ or an ester of $R_1$, such as $CH_2CH_2C(O)OCH_3$. In a most preferred embodiment, $R_2$ is $CH_3$ or $CH_2CH_3$.

$R_3$ are each independently halogen, halogen radioisotope or $R_2$. Preferred halogens include fluorine and chlorine. The variable n is an integer from 0 to 5. In a preferred embodiment, n ranges from 0-3, and is most preferably 0.

$R_4$ and $R_5$ are independently H, halogen, CN or $CF_3$. Preferably, none or at least one of $R_4$ and $R_5$ is halogen, CN or $CF_3$. More preferably, at least one of $R_4$ and $R_5$ is Br or CN.

The linkers $L_1$ and $L_2$ are each independently a bond, a substituted or unsubstituted $C_1$-$C_{10}$ alkylene, $C_2$-$C_{10}$ alkenylene, or $C_2$-$C_{10}$ alkynylene group. The backbone of alkylene may contain one or more heteroatoms, such as O, N, or S. Preferably, $L_1$ and $L_2$ are each independently a bond or a linear $C_1$-$C_4$ alkylene group. Most preferably, $L_1$ is a bond or $CH_2CH_2$, and $L_2$ is $CH_2CH_2$, $CH_2(CH_2)_4CH_2$, or $CH_2CH_2O(CH_2)_3$. In a most preferred embodiment, $L_2$ is $CH_2CH_2$.

The tail T may be H, a substituted or unsubstituted $C_1$-$C_{10}$ alkyl, $C_2$-$C_{10}$ alkenyl, or $C_2$-$C_{10}$ alkynyl. The backbone of alkyl may contain one or more heteroatoms, such as O, N, or S. The tail may also be cyclopropyl, nitrophenol, or any other suitable electron withdrawing group. Preferably, T is a $C_1$-$C_4$ alkyl group. Most preferably T is $CH_3$, $CH_2CH_3$, $CH_2CH_2CH_2CH_3$, $CH_2CH(OH)CH_3$ or $CH_2CH_2OCH_3$. In a most preferred embodiment, T is $CH_3$. In another most preferred embodiment, T is nitrophenol. In yet another preferred embodiment T is H. In yet still another preferred embodiment, T is $CH_2CH(OH)CH_3$.

The compounds of formula (I) include pharmaceutically acceptable salts, stereoisomer mixtures, and enantiomers thereof. The compounds of the invention also include physiologically acceptable salts of the compounds of formula (I). Preferred physiologically acceptable salts are acid-addition salts known to those of skill in the art. Common physiologically acceptable acid-addition salts include but are not limited to, hydrochloric acid salts, oxalate salts, and tartrate salts.

In certain embodiments of the compound, $R_1$ is $L_1C(O)OT$, $R_2$ is $CH_3$, n is 0, $L_1$ is a bond, and T is $CH_2CH_3$.

In other embodiments of the compound, $R_1$ is $L_1C(O)OT$, $R_2$ is $CH_3$, n is 0, $L_1$ is a bond, and T is $CH_3$.

In yet still other embodiments of the compound, $R_1$ is $L_1C(O)OT$, $R_2$ is $CH_3$, n is 0, $L_1$ is a bond, and T is H.

In a preferred embodiment of the compound $R_1$ is $L_1C(O)OT$, $R_2$ is $CH_3$, n is 0, $L_1$ is a bond, $R_4$ is H, $R_5$ is H and T is $CH_2CH_3$.

In another preferred embodiment of the compound, $R_1$ is $L_1C(O)OT$, $R_2$ is $CH_3$, n is 0, $L_1$ is a bond, $R_4$ is H, $R_5$ is Br or CN and T is $CH_2CH_3$.

In still another preferred embodiment of the compound $R_1$ is $L_1C(O)OT$, $R_2$ is $CH_3$, n is 0, $L_1$ is a bond, $R_4$ is Br or CN, $R_5$ is H and T is $CH_2CH_3$.

In yet still another preferred embodiment of the compound $R_1$ is $L_1C(O)OT$, $R_2$ is $CH_3$, n is 0, $L_1$ is a bond, $R_4$ is H, $R_5$ is H and T is $CH_2CH(OH)CH_3$.

In yet still another preferred embodiment of the compound $R_1$ is $L_1C(O)OT$, $R_2$ is $CH_3$, n is 0, $L_1$ is a bond, $R_4$ is H, $R_5$ is H and T is H.

In still yet other embodiments of the compound, $R_1$ is $L_1C(O)OT$, $R_2$ is $CH_2CH_3$, n is 0, $L_1$ is a bond, and T is $CH_3$.

In other embodiments of the compound, $R_1$ is $L_1C(O)OT$, $R_2$ is $CH_2CH_3$, n is 0, $L_1$ is a bond, and T is $CH_2CH_3$.

In certain embodiments of the compound, $R_1$ is $L_1C(O)OT$, $R_2$ is $CH_3$, n is 1-5, each $R_3$ independently is halogen, $L_1$ is a bond, and T is $CH_2CH_3$.

In other embodiments of the compound, $R_1$ is $L_1C(O)OT$, $R_2$ is $CH_3$, n is 1-5, each $R_3$ is fluorine, $L_1$ is a bond, and T is $CH_2CH_3$.

In still yet other embodiments of the compound, $R_1$ is $L_1C(O)OT$, $R_2$ is $CH_2CH_3$, n is 1, $R_3$ is fluorine, $L_1$ is a bond, and T is $CH_2CH_3$.

In another preferred embodiment of the compound, $R_1$ is $L_1C(O)OL_2C(O)OT$, $R_2$ is $CH_3$, n is 0, $L_1$ is a bond, $L_2$ is $CH_2CH_2$, and T is $CH_3$.

In certain embodiments of the compound, $R_1$ is $L_1C(O)OL_2C(O)OT$, $R_2$ is $CH_3$, n is 0, $L_1$ is a bond, $L_2$ is $CH_2(CH_2)_4CH_2$, and T is $CH_2CH_2CH_2CH_3$.

In other embodiments of the compound, $R_1$ is $L_1C(O)OL_2C(O)OT$, $R_2$ is $CH_3$, n is 0, $L_1$ is a bond, $L_2$ is $CH_2CH_2O(CH_2)_3$, and T is $CH_2CH_2OCH_3$.

In certain embodiments of the compound, $R_1$ is $L_1C(O)OL_2C(O)OT$, $R_2$ is $CH_3$, each $R_3$ independently is halogen, n is 1-5, $L_1$ is a bond, $L_2$ is $CH_2CH_2$, and T is $CH_3$.

In other embodiments of the compound, $R_1$ is $L_1C(O)OL_2C(O)OT$, $R_2$ is $CH_3$, each $R_3$ independently is halogen, n is 1-5, $L_1$ is a bond, $L_2$ is $CH_2(CH_2)_4CH_2$, and T is $CH_2CH_2CH_2CH_3$.

In still yet other embodiments of the compound, $R_1$ is $L_1C(O)OL_2C(O)OT$, $R_2$ is $CH_3$, each $R_3$ independently is halogen, n is 1-5, $L_1$ is a bond, $L_2$ is $CH_2CH_2O(CH_2)_3$, and T is $CH_2CH_2OCH_3$.

In further embodiments of the compound, $R_1$ is $L_1C(O)OT$, $R_2$ is $CH_3$, at least one $R_3$ is $CH_2CH_2C(O)OCH_3$, $L_1$ is a bond, and T is $CH_2CH_3$.

In still yet further embodiments of the compound, $R_1$ is $L_1C(O)OL_2C(O)OT$, $R_2$ is $CH_3$, at least one $R_3$ is $CH_2CH_2C(O)OCH_3$, $L_1$ is a bond, $L_2$ is $CH_2CH_2$, and T is $CH_3$.

In a preferred embodiment of the compound, $R_1$ is $L_1C(O)OT$, $R_2$ is $CH_2CH_2C(O)OCH_3$, n is 0, $L_1$ is a bond, and T is $CH_2CH_3$.

In another preferred embodiment of the compound, $R_1$ is $L_1C(O)OT$, $R_2$ is $CH_3$, n is 0, $L_1$ is $CH_2CH_2$, and T is $CH_2CH_3$.

In some embodiments, the compound of formula (I) is selected from the group consisting of

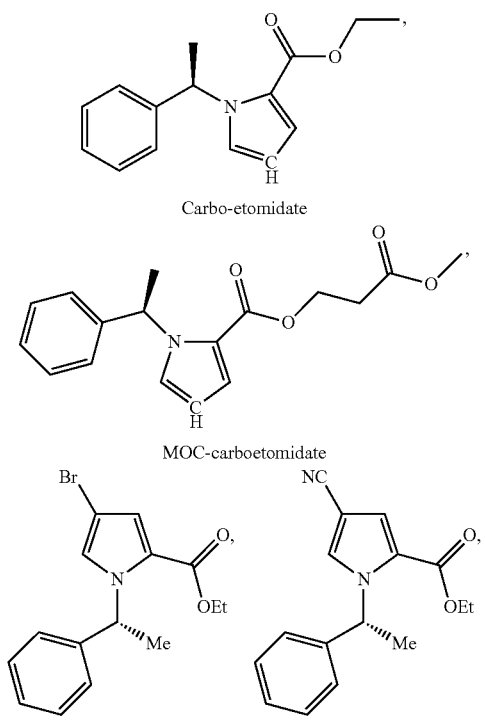

Carbo-etomidate

MOC-carboetomidate

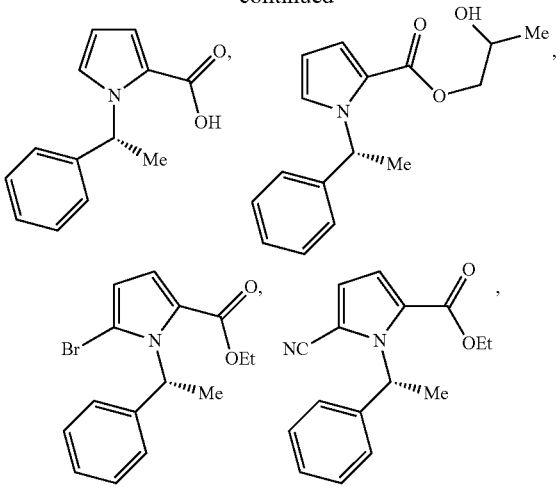

and pharmaceutically acceptable salts, stereoisomer mixtures, and enantiomers thereof.

The carbon atom bridging the 6-membered ring and the 5-membered ring is a chiral center. Therefore, the compound may be in the form of a pure enantiomer. In a preferred embodiment, the enantiomer is the R enantiomer. In another embodiment, the enantiomer is the S enantiomer.

Compounds of formula (I) preferably have the same stereochemistry as (R)-etomidate. $R_2$, $R_3$, $L_1$, $L_2$, and T can be branched hydrocarbon chains, however, not to the extent that steric hindrance or conjugation interferes with the desired activity.

In certain embodiments, the compound includes two or more ester groups. Suitable ester-containing groups (e.g. linker-ester-tail or ester-tail) can be added to the bridging carbon or at various positions of the phenyl ring or the core molecule.

Rapidly metabolized etomidate analogues with ester moieties on carboetomidate that are sterically unhindered and/or electronically isolated from the pi electron systems in the imidazole and phenyl rings are also preferred. Such ester moieties, like those in other ultra-short acting drugs like remifentanil and esmolol, are believed to be highly susceptible to hydrolysis by esterases. See U.S. Pat. Nos. 3,354,173; 5,466,700; 5,019,583; and U.S. Patent Publication No. US 2003/0055023.

The $R_2$, T, $L_1$, and $L_2$ substituents may each independently be substituted with one or more electron withdrawing groups. In a certain embodiments, the electron withdrawing group is a halogen, nitrophenol, or cyclopropyl. Other electron withdrawing groups such as hydroxy groups, amino groups, nitro groups, nitrile groups, sulfonate groups, carboxylate groups, halide groups, mercaptan groups, and unsaturated alkyl groups, may also be used. The presence of electron withdrawing groups serves to increase the partial positive charge on the ester carbonyl atom, thereby increasing susceptibility to nucleophilic attack by esterases and further enhancing rapid hydrolysis by esterases.

The compounds of the invention have demonstrated anesthetic and enhanced $GABA_A$ receptor activities. Compounds of the invention uniformly demonstrated potent in vitro and in vivo anesthetic and enhanced $GABA_A$ receptor effects. These results indicate that compounds of the invention are highly active agents with potent in vitro and in vivo activities. Importantly, the compounds have reduced inhibitory activity with respect to in vitro and in vivo adrenocortical steroid synthesis and/or short durations of anesthetic action.

The compounds described above can either be administered alone in the form of mixtures with one another, or in combination with acceptable pharmaceutical carriers. The invention, thus, also relates to pharmaceutical compositions which comprise an effective amount of at least one compound of the invention with or without a pharmaceutically or physiologically acceptable carrier. If appropriate, the compound may be administered in the form of a physiologically acceptable salt, for example, an acid-addition salt.

The invention also encompasses a method of treating animals or humans. This method comprises administering to the animal or person an effective amount of at least one of the compounds of the invention, or a pharmaceutically acceptable salt thereof, with, or without a pharmaceutically acceptable carrier. Intravenous administration is preferred. See U.S. Pat. No. 4,289,783, which is hereby incorporated by reference in its entirety.

The invention is a potent sedative hypnotic that does not significantly suppress adrenocortical function and may be used to produce and/or maintain anesthesia, sedation, or otherwise lower central nervous system excitability. It exhibits one or more of the following beneficial properties as compared to alternative agents: higher potency, shorter duration of therapeutic action, shorter duration of side effects, reduced adrenocortical suppression, higher therapeutic index, lower toxicity, reduced cardiovascular depression, and greater ease of titration to desired effect. The invention may be administered as a single IV bolus or a continuous IV infusion. Other route of delivery may include oral, rectal, transmucosal, subcutaneous, or inhaled.

Pharmaceutical Compositions

For administration to a subject, the compounds described herein can be provided in pharmaceutically acceptable compositions. Accordingly, another aspect of the invention is directed to a pharmaceutical composition comprising a compound according to formula (I) and a pharmaceutically acceptable carrier. These pharmaceutically acceptable compositions comprise an effective amount of one or more of the compounds described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous (e.g., bolus or infusion) or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally.

In some embodiments, the compounds of the present invention can be used in the form of a pharmaceutically acceptable salt. Suitable acids which are capable of forming salts with the compounds of the invention include inorganic acids such as hydrochloric acid, hydrobromic acid, perchloric acid, nitric acid, thiocyanic acid, sulfuric acid, phosphoric acid, and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, trifluoroacetic acid, methansulfonic acid, benzenesulfonic acid, p-toulenesulfonic acid, and the like. Suitable bases capable of forming salts with the compounds of the invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine, pyridine, picoline, dicyclohexylamine, N,N'-dibezylethylenediamine, and the like) and optionally substituted ethanol-amines (e.g., ethanolamine, diethanolamine, trierhanolamine and the like).

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions, or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As indicated above, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

It is especially advantageous to formulate oral and intravenous compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. The pharmaceutical compositions can be included in a container, pack, or dispenser together with instructions for administration. A pharmaceutical composition typically contains an amount of at least 0.01 weight % of active ingredient, i.e., a compound of this invention, per weight of total pharmaceutical composition. A weight % is a ratio by weight of active ingredient to total composition. Thus, for example, 0.1 weight % is 0.1 grams of the compound per 100 grams of total composition.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic, or oily solutions and the like as detailed above.

For intravenous administration, Glucuronic acid, L-lactic acid, acetic acid, citric acid or any pharmaceutically acceptable acid/conjugate base with reasonable buffering capacity in the pH range acceptable for intravenous administration can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12.

Subcutaneous formulations can be prepared according to procedures well known in the art at a pH in the range between about 5 and about 12, which include suitable buffers and isotonicity agents. They can be formulated to deliver a daily dose of the active agent in one or more daily subcutaneous administrations. The choice of appropriate buffer and pH of a formulation, depending on solubility of one or more compounds to be administered, is readily made by a person having ordinary skill in the art. Sodium chloride solution wherein the pH has been adjusted to the desired range with either acid or base, for example, hydrochloric acid or sodium hydroxide, can also be employed in the subcutaneous formulation. Typically, a pH range for the subcutaneous formulation can be in the range of from about 5 to about 12.

Methods of the Invention

Yet another aspect of the invention is directed to a method for providing anesthesia in a subject including administering to the subject a pharmaceutical composition substantially the same as described above. Accordingly, in certain embodiments, the method includes administering an effective dose of the compound. The effective dose comprises 0.01 to 100 mg/kg of the compound. As used herein, the term "effective dose" or "effective amount" is meant that amount sufficient to elicit the desired pharmacological effects. The actual effective amount will of course vary with the specific compound, the application technique, the desired effect, and the duration of the effect and side effects, and may be readily determined by the practitioner skilled in the art. Thus an effective dose of compound described herein is an amount sufficient to induce and maintain general anesthesia or conscious sedation in a subject.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

Generally, the compositions are administered so that a compound of the invention is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

The terms "administration of" and or "administering" a compound should be understood to mean providing a compound or a composition of the invention to a subject in need of inducing anesthesia. As such, the term "administer" refers to the placement of a compound or composition of the invention into a subject by a method or route which results in at least partial localization of the compound or composition at a desired site such that general anesthesia or conscious sedation is induces and/or maintained in the subject.

The compounds described herein can be administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection.

In a preferred embodiment, the method includes administering an injection of a single effective dose of the compound which may or may not be followed by a continuous infusion of the compound.

In certain embodiments, the method includes administering a continuous infusion of an effective dose of the compound of formula (I).

The compounds described herein can be administrated to a subject in combination with another pharmaceutically active agent or treatment modality for a particular indication. Exemplary pharmaceutically active compound include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Accordingly, in certain embodiments, the method also includes administering to the subject an effective amount of a therapeutic agent selected from another sedative hypnotic agent, an analgesic agent, and a paralytic agent. Non-limiting examples of sedative hypnotic agents include benzodiazepines, barbiturates, ketamine, propofol, isoflurane, and desflurane. Non-limiting examples of analgesic agents include non-steroidal anti-inflammatory drugs (NSAIDs), paracetamol/acetaminophen, COX-2 inhibitors, and opioids. Non-limiting examples of paralytic agents include rapacuronium, mivacurium, succinylcholine, vecuronium, and cisatracurium.

As used herein, a "subject" means a marnamal, e.g., a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. In certain embodiments, the subject is a mammal.

Synthesis of Compounds of the Invention

The compounds according to the invention may be prepared by synthetic processes which are known to those skilled in the art, particularly in view of the state of the art and the specific preparatory examples provided below herein. Suitable modification to starting materials by methods well known in the art may also be employed.

The compounds according to the invention may be prepared by a process which comprises coupling a phenyl of formula (II):

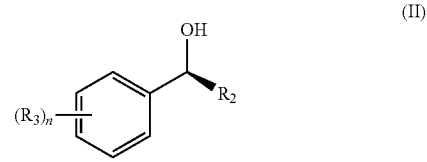

(II)

wherein, $R_2$ is a substituted or unsubstituted $C_1$-$C_{10}$ alkyl, $C_2$-$C_{10}$ alkenyl, or $C_2$-$C_{10}$ alkynyl, or $R_1$;

n is an integer from 0-5;

each $R_3$ is independently halogen or $R_2$;

with a pyrrole of formula (III):

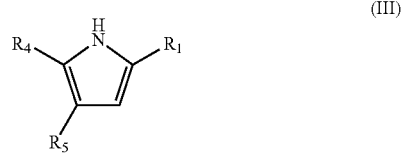

wherein,
$R_1$ is $L_1C(O)OT$ or $L_1C(O)OL_2C(O)OT$;
$R_4$ and $R_5$ are independently H, halogen, CN or $CF_3$;
$L_1$ and $L_2$ are each independently a bond, a substituted or unsubstituted $C_1$-$C_{10}$ alkylene, $C_2$-$C_{10}$ alkenylene, or $C_2$-$C_{10}$ alkynylene, wherein the backbone of alkylene may contain one or more heteroatoms; and
T is H, a substituted or unsubstituted $C_1$-$C_{10}$ alkyl, $C_2$-$C_{10}$ alkenylene, $C_2$-$C_{10}$ alkynylene, nitrophenol, or cyclopropyl, wherein the backbone of alkyl may contain one or more heteroatoms.

The reaction between phenyl of formula (II) and pyrrole of formula (III) proceeds with inversion of configuration to give compounds of formula (I). The phenyls of formula (II) are easily prepared by reduction of phenyl alkyl ketones and derivatives thereof.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the term "alkyl" refers to saturated straight-chain, branched-chain or cyclic hydrocarbon radicals. Examples of alkyl radicals include, but are not limited to, methyl, ethyl, propyl, isopropyl, cyclopropyl-, n-butyl, tert-butyl, neopentyl, n-hexyl, cyclohexyl, n-octyl, n-decyl, n-dodecyl and n-hexadecyl radicals.

As used herein, the term "alkenyl" refers to unsaturated straight-chain, branched-chain or cyclic hydrocarbon radicals having at least one carbon-carbon double bond. Examples of alkenyl radicals include, but are not limited to, allyl, butenyl, hexenyl and cyclohexenyl radicals.

As used herein, the term "alkynyl" refers to unsaturated hydrocarbon radicals having at least one carbon-carbon triple bond. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

As used herein, the term "halogen" refers to an atom selected from fluorine, chlorine, bromine and iodine. The term "halogen radioisotope" refers to a radionuclide of an atom selected from fluorine, chlorine, bromine and iodine.

As used herein, the term "substituted" refers to independent replacement of one or more of the hydrogen atoms on the substituted moiety with substituents independently selected from, but not limited to, alkyl, alkenyl, heterocycloalkyl, alkoxy, aryloxy, hydroxy, amino, amido, alkylamino, arylamino, cyano, halo, mercapto, nitro, carbonyl, acyl, aryl and heteroaryl groups.

The present invention can be defined in any of the following numbered paragraphs:

1. A compound according to formula (I)

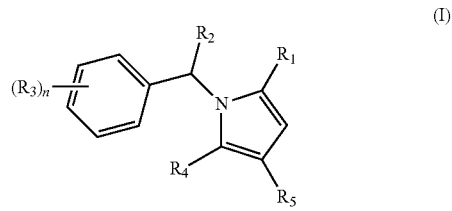

wherein,
$R_1$ is $L_1C(O)OT$ or $L_1C(O)OL_2C(O)OT$;
$R_2$ is a substituted or unsubstituted $C_1$-$C_{10}$ alkyl, $C_2$-$C_{10}$ alkenyl, or $C_2$-$C_{10}$ alkynyl, or $R_1$;

n is an integer from 0-5;

each $R_3$ is independently halogen or $R_2$;

$R_4$ and $R_5$ are independently H, halogen, CN or $CF_3$;

$L_1$ and $L_2$ are each independently a bond, a substituted or unsubstituted $C_1$-$C_{10}$ alkylene, $C_2$-$C_{10}$ alkenylene, or $C_2$-$C_{10}$ alkynylene, wherein the backbone of alkylene may contain one or more heteroatoms;

T is H, a substituted or unsubstituted $C_1$-$C_{10}$ alkyl, $C_2$-$C_{10}$ alkenylene, $C_2$-$C_{10}$ alkynylene, nitrophenol, or cyclopropyl, wherein the backbone of alkyl may contain one or more heteroatoms; and pharmaceutically acceptable salts, stereoisomer mixtures, and enantiomers thereof.

2. The compound of paragraph 1, wherein said compound is present in the form of a pure enantiomer.

3. The compound of paragraph 2, wherein said enantiomer is the R enantiomer.

4. The compound of any of paragraphs 1-3, wherein $R_1$ is $L_1C(O)OT$.

5. The compound of any of paragraphs 1-3, wherein $R_1$ is $L_1C(O)OL_2C(O)OT$.

6. The compound of any of paragraphs 1-5, wherein $R_2$ is selected from the group consisting of $CH_3$, $CH_2CH_3$ and $CH_2CH_2CH_3$.

7. The compound of any of paragraphs 1-6, wherein T is selected from the group consisting of H, $CH_3$, $CH_2CH_3$, $CH_2CH(OH)CH_3$, and $CH_2CH_2CH_3$.

8. The compound of any of paragraphs 1-7, wherein n is 0 or 1.

9. The compound of any of paragraphs 1-8, wherein $R_2$ is $CH_3$, n is 0, $L_1$ is a bond, and T is H, $CH_3$, $CH_2CH_3$, or $CH_2CH(OH)CH_3$.

10. The compound of any of paragraphs 1-9, wherein both $R_4$ and $R_5$ are H.

11. The compound of any of paragraphs 1-9, wherein at least one of $R_4$ and $R_5$ is H and the other is Br or CN.

12. The compound of paragraph 11, wherein $R_4$ is H and $R_5$ is Br or CN.

13. The compound of paragraph 11, wherein $R_4$ is Br or CN and $R_5$ is H.

14. The compound of paragraph 1, wherein the compound of formula (I) is selected from the group consisting of

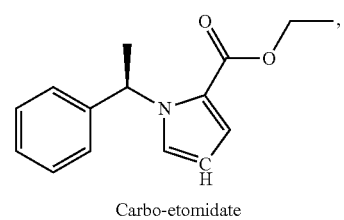
Carbo-etomidate

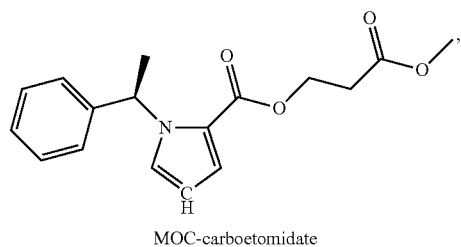
MOC-carboetomidate

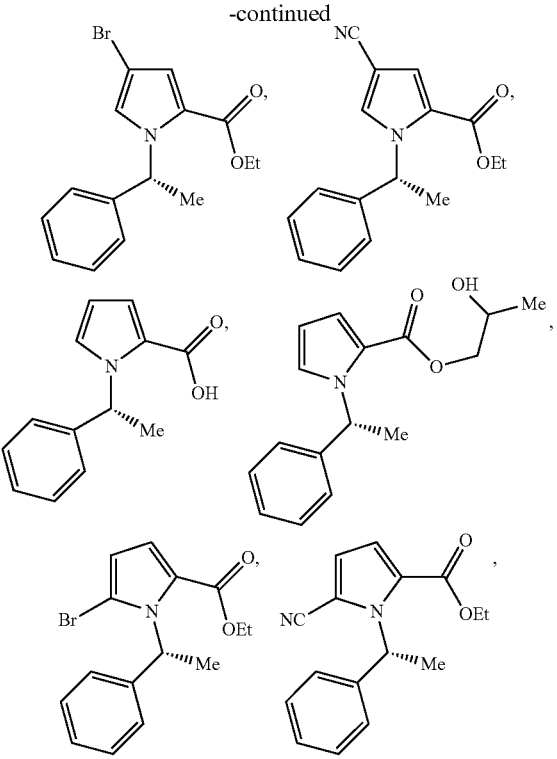

and pharmaceutically acceptable salts, stereoisomer mixtures, and enantiomers thereof.

15. A pharmaceutical composition comprising a pharmaceutically effective amount of a compound of any of paragraphs 1-14 and a pharmaceutically acceptable carrier.

16. A method for providing anesthesia to a subject comprising administering to said subject a pharmaceutical composition according to paragraph 15.

17. A method for providing anesthesia to a subject comprising administering to said subject a compound of formula (I) according to paragraphs 1-14.

18. The compound of any of paragraphs 1-14 for use for providing anesthesia to a subject.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLES

The invention is further illustrated by the following examples which should not be construed as limiting. The examples are illustrative only, and are not intended to limit, in any manner, the claimed invention.

Materials and Methods

Animals: All animal studies were conducted in accordance with rules and regulations of the Subcommittee on Research Animal Care at the Massachusetts General Hospital, Boston, Mass. Early prelimb-bud stage *Xenopus laevis* tadpoles and adult female *Xenopus laevis* frogs were purchased from *Xenopus* 1 (Ann Arbor, Mich.). Tadpoles were maintained in our laboratory, and frogs were maintained in the Massachusetts General Hospital Center for Comparative Medicine animal care facility. Adult male Sprague-Dawley rats (300-500 g) were purchased from Charles River Laboratories (Wilmington, Mass.) and housed in the Massachusetts General Hospital Center for Comparative Medicine animal care facility. Blood draws and IV drug administrations used a lateral tail vein IV catheter (24 gauge, 19 mm) placed under brief (approximately 1-5 min) sevoflurane or isoflurane anesthesia delivered using an agent specific variable bypass vaporizer with continuous gas monitoring. Animals were weighed immediately before IV catheter placement and were allowed to fully recover from inhaled anesthetic exposure before study. In all studies, rats were placed on a warming stage (Kent Scientific, Torrington, Conn.) that was shown in previous studies to maintain rectal temperatures between 36° and 38° C. in anesthetized rats. See for example Cotton et al., Anesthesiology, (2009) 111: 240-249, content of which is herein incorporated by reference.

Loss of Righting Reflex

Tadpoles: Groups of five early prelimb-bud stage *Xenopus laevis* tadpoles were placed in 100 ml of oxygenated water buffered with 2.5 mM Tris HCl buffer (pH. 7.4) and containing a concentration of carboetomidate ranging from 1 to 40 J M. Tadpoles were tipped manually every 5 min with a flame-polished pipette until the response stabilized. Tadpoles were judged to have loss of righting reflex (LORR) if they failed to right themselves within 5 s after being turned supine. At the end of each study, tadpoles were returned to fresh water to ensure reversibility of hypnotic action. The EC50 for LORR was determined from the carboetomidate concentration dependence of LORR using the method of Waud D R, J Pharmacol Exp Ther (1972) 183: 577-607, content of which is herein incorporated by reference.

Rats: Rats were briefly restrained in a 3-inch diameter, 9-inch long acrylic chamber with a tail exit port. The desired dose of carboetomidate in dimethyl sulfoxide (DMSO; typically at 40 mg/ml) was injected through a lateral tail vein catheter followed by an approximately 1-ml normal saline flush. After injection, rats were removed from the restraint device and turned supine. A rat was judged to have LORR if it failed to right itself (onto all four paws) after drug administration. A stopwatch was used to measure the duration of LORR, which was defined as the time from carboetomidate injection until the animal spontaneously righted itself. The ED50 for LORR on bolus administration was determined from the dose dependence of LORR using the method of Waud.26 Onset time for LORR was determined separately by injecting rats with 28 mg/kg of carboetomidate (40 mg/ml in DMSO) or 4 mg/kg of etomidate (5.7 mg/ml in DMSO) through a lateral tail vein catheter followed by an approximately 1-ml normal saline flush. After injection, rats were immediately removed from the restraint device and repeatedly turned supine until they no longer spontaneously righted. The onset time was defined as the time from injection until LORR occurred.

GABAA Receptor Electrophysiology

Adult female *Xenopus laevis* frogs were anesthetized with 0.2% tricaine (ethyl-m-aminobenzoate) and hypothermia. Ovary lobes were then excised through a small laparotomy incision and placed in OR-2 solution (82 mM NaCl, 2 mM KCl, 2 mM $MgCl_2$, 5 mM HEPES, pH 7.5) containing collagenase 1A (1 mg/ml) for 3 h to separate oocytes from connective tissue.

Stage 4 and 5 oocytes were injected with messenger RNA encoding the $\alpha_1$, $\beta_2$ (or $\beta_2$M286W), and $\gamma_{21}$ subunits of the human $GABA_A$ receptor (~40 ng of messenger RNA total at a subunit ratio of 1:1:2). This messenger RNA was transcribed from complementary DNA encoding for GABAA receptor $\alpha_1$, $\beta_2$ (or $\beta_2$M286W), and $\gamma_{21}$ subunits using the mMES-SAGE mMACHINE High Yield Capped RNA Transcription Kit (Ambion, Austin, Tex.). Injected oocytes were incubated in ND-96 buffer solution (96 mM NaCl, 2 mM KCl, 1 mM $CaCl_2$, 0.8 mM $MgCl_2$, 10 mM HEPES, pH 7.5) containing 50 U/ml of penicillin and 50 μg/ml of streptomycin at 17° C. for at least 18 h before electrophysiologic experiments.

All electrophysiologic recordings were performed using the whole cell two-electrode voltage-clamp technique. Oocytes were placed in a 0.04-ml recording chamber and impaled with capillary glass electrodes filled with 3 M KCl and possessing open tip resistances less than 5 MΩ. Oocytes were then voltage clamped at −50 mV using a Gene-Clamp 500B amplifier (Axon Instruments, Union City, Calif.) and perfused with ND-96 buffer at a rate of 4-6 ml/min. Buffer perfusion was controlled using a six-channel valve controller (Warner Instruments, Hamden, Conn.) interfaced with a Digidata 1322A data acquisition system (Axon Instruments) and driven by a Dell personal computer (Round Rock, Tex.). Current responses were recorded using Clampex 9.2 software (Axon Instruments) and processed using a Bessel (8-pole) low-pass filter with a cutoff at 50 Hz using Clampfit 9.2 software (Axon Instruments).

For each oocyte, the concentration of GABA that produces 5-10% of the maximal current response ($EC_{5-10}$ GABA) was determined by measuring the peak current responses evoked by a range of GABA concentrations (in ND-96 buffer) and comparing them with the maximal peak current response evoked by 1 mM GABA. The effect of carboetomidate on $EC_{5-10}$ GABA-evoked currents was then assessed by first perfusing the oocyte with $EC_{5-10}$ GABA for 90 s and then measuring the control peak evoked current. After a 5-min recovery period, the oocyte was perfused with carboetomidate for 90 s and then with $EC_{5-10}$ GABA plus carboetomidate for 90 s, and the peak evoked current was measured again. After a 15-min recovery period, the control experiment (i.e., no carboetomidate) was repeated to test for reversibility. A longer recovery period after carboetomidate exposure was used to facilitate washout of the drug. The peak current response in the presence of carboetomidate was then normalized to the average peak current response of the two control experiments. Carboetomidate-induced potentiation was quantified from the normalized current responses in the presence versus absence of carboetomidate.

Rat Hemodynamics

The effects of hypnotics on rat hemodynamics were defined as described previously in Cotton et al., Anesthesiology, (2009) 111: 240-249. Femoral arterial catheters, tunneled between the scapulas, were preimplanted by the vendor (Charles River Laboratories). Animals were fully recovered from the placement procedure on arrival. During housing and between studies, catheter patency was maintained with a heparin (500 U/ml) and hypertonic (25%) dextrose locking solution, which was withdrawn before each use and replaced just after.

On the day of study, after weighing and lateral tail vein IV catheter placement, rats were restrained in the acrylic tube with a tail exit port and allowed to acclimate for approximately 10 to 20 min before data collection. The signal from the pressure transducer (TruWave, Edwards Lifesciences, Irvine, Calif.) was amplified using a custom-built amplifier (AD620 operational amplifier, Jameco Electronics, Belmont, Calif.) and digitized (1 kHz) using a USB-6009 data acquisition board (National Instruments, Austin, Tex.) without additional filtering. All data were acquired and analyzed using LabView Software (version 8.5 for Macintosh OS X; National Instruments).

Data used for blood pressure analysis were recorded for 5 min immediately before hypnotic administration and for 15 min thereafter. Carboetomidate (40 mg/ml) dissolved in DMSO, etomidate (5.7 mg/ml) dissolved in DMSO, or DMSO vehicle alone as a control was administered through the tail vein catheter followed by approximately 1-ml normal saline flush.

Inhibition of In Vitro Cortisol Synthesis

In vitro cortisol synthesis was measured using the human adrenocortical cell line H295R(NCI-H295R; ATCC CRL2128). Aliquots of $10^5$ cells per well were grown in 12-well culture plates with 2 ml of growth medium (Dulbecco's Modified Eagle Medium/F12 supplemented with 1% insulin, transferrin, selenium, and linoleic acid, 2.5% NuSerum, and Pen/Strep). When cells reached near confluence (typically 48-72 h), the growth medium was replaced with assay medium (Dulbecco's Modified Eagle Medium/F12 supplemented with 0.1% insulin, transferring, selenium containing antibiotics and 20 µM forskolin) that contained etomidate or carboetomdiate. After 48 h, 1.2 ml of assay medium was collected from each well, centrifuged to pellet any cells or debris, and the cortisol concentration in the supernatant was quantified by enzyme-linked immunosorbent assay using commercially available 96-well kits based on horseradish peroxidase-conjugated cortisol in a competitive antibody binding assay (R&D Systems, Minneapolis, Minn., KGE008).

Rat Adrenocortical Suppression

Immediately after weighing and IV catheter placement, dexamethasone (0.2 mg/kg IV; American Regent, Shirley, N.Y.) was administered to each rat to inhibit endogenous adrenocorticotropic hormone (ACTH) release, to suppress baseline corticosterone production, and to inhibit the variable stress response to restraint and handling. Two hours after dexamethasone treatment, blood was drawn (for baseline measurement of serum corticosterone concentration), and a second dose of dexamethasone (0.2 mg/kg) was administered along with IV carboetomidate, etomidate, or DMSO vehicle as a control. The concentrations of carboetomidate and etomidate in DMSO were 40 and 5.7 mg/ml, respectively. Immediately after hypnotic or vehicle administration, $ACTH_{1-24}$ (25 µg/kg; Sigma-Aldrich Chemical Co, St. Louis, Mo.) was given intravenously to stimulate corticosterone production. Fifteen minutes later, a second blood sample was drawn to measure the $ACTH_{1-24}$-stimulated serum corticosterone concentration. $ACTH_{1-24}$ was dissolved in 1 mg/ml of deoxygenated water as stock, aliquoted, and frozen (−20° C.); a fresh aliquot was thawed just before each use. Rats in all three groups (carboetomidate, etomidate, and vehicle) received the same volume of DMSO (350 µl/kg).

Corticosterone concentrations in blood serum were determined as reported previously in Cotton et al., Anesthesiology, (2009) 111: 240-249. Blood samples were allowed to clot at room temperature (10-60 min) before centrifugation at 3,500 g for 5 min. Serum was carefully expressed from any resulting superficial fibrin clot using a clean pipette tip before a second centrifugation at 3,500 g for 5 min. After the second centrifugation, the resultant clot-free serum layer was transferred to a fresh vial for a final, high-speed centrifugation (16,000 g, for 5 min) to pellet any contaminating red blood cells or particulates. The serum was transferred to a clean vial and promptly frozen (−20° C.) pending corticosterone measurement. After thawing and heat inactivation of corticosterone-binding globulins (65° C. for 20 min), serum baseline and $ACTH_{1-24}$-stimulated corticosterone concentrations were quantified using an enzyme-linked immunosorbent assay (Diagnostic Systems Laboratories, Webster, Tex.) and a 96-well plate reader (Molecular Devices, Sunnyvale, Calif.).

Statistical Analysis

All data are reported as mean±SD. Statistical analysis and curve fitting (using linear or nonlinear least squares regression) were performed using either Prism v4.0 for the Macintosh (GraphPad Software, Inc., LaJolla, Calif.) or Igor Pro 4.01 (Wavemetrics, Lake Oswego, Oreg.). $P<0.05$ indicates statistical significance unless otherwise indicated. For multiple comparisons of physiologic data derived from rats, we performed a one-way or two-way ANOVA followed by a Bonferroni posttest (which relies on an unpaired t test with a Bonferroni correction).

Example 1

Synthesis of (R)-1-(1-phenylethyl)-1H-pyrrole-2-carboxylate (carboetomidate)

A solution of (S)-1-phenylethanol (135 mg, 1.10 mmol) in dry THF (2 mL) was added dropwise to a stirred solution of ethyl 1H-pyrrole-2-carboxylate (140 mg, 1.00 mmol) and triphenylphosphine (340 mg, 1.30 mmol) in dry THF (3 mL) in an atmosphere of argon at room temperature. Then a solution of di-tert-butyl azodicarboxylate (304 mg, 1.32 mmol) in dry THF (2 mL) was added, and the reaction mixture was allowed to stir at room temperature over-night. The reaction mixture was concentrated under reduced pressure. The residue was mixed with diethyl ether (5 mL) and stirred for 2 h. The residue ($Ph_3PO$ and hydrazo ester) were collected and washed with diethyl ether (3×2 mL). The filtrate was evaporated under reduced pressure to yield a residue, which was purified by flash chromatography (hexanes/$CH_2Cl_2$=7:3) on silica gel to give a colorless viscous liquid: IR (KBr, cm$^{-1}$): 737, 1106, 1231, 1700, 2980, 3328; $^1$H NMR (500 MHz, CDCl$_3$): δ 1.30 (t, J=7.5 Hz, 3H), 1.80 (d, J=7.0 Hz, 3H), 4.17-4.28 (m, 2H), 6.17 (dd, J=4.0, 3.0 Hz, 1H), 6.60 (q, J=7.0 Hz, 1H), 6.98-7.01 (m, 2H), 7.12-7.14 (m, 2H), 7.20-7.25 (m, 1H), 7.28-7.32 (m, 2H); $^{13}$C NMR (500 MHz, CDCl$_3$): δ 14.6, 22.3, 55.5, 60.0, 108.5, 118.5, 122.6, 125.5, 126.4, 127.5, 128.7, 143.3, 161.4; LC-MS obsd 244.10, calcd 244.10 for C15H18NO2 (M+H); Analytical calculation for C, 74.05; H, 7.04; N, 5.76. Found: C, 74.25; H, 6.94; N, 5.66. The final product was determined to be essentially enantiomerically pure (R-enantiomer) by chiral column chromatography. See Scheme 1.

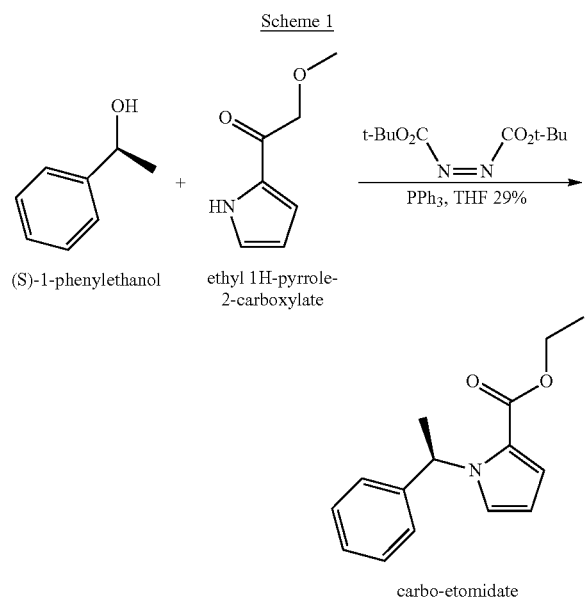

Scheme 1

Example 2

Carboetomidate is a Potent General Anesthetic in Tadpoles and Rats

Tadpoles: The tadpole loss of righting reflex assay was used to test for anesthetic activity. Groups of 5 early prelimb-bud stage *Xenopus laevis* tadpoles were placed in 100 ml of oxygenated water buffered with 2.5 mM Tris HCl buffer (pH=7) and containing a concentration of carboetomidate ranging from 1-40 μM. See Scheme 1, above, for structure of Carboetomidate. Tadpoles were tipped manually every 5 min with a flame polished pipette. Tadpoles were deemed to be anesthetized (have loss of righting reflex (LORR)) if they failed to right themselves within 5 sec. At all concentrations, this loss of righting reflex response stabilized within 30 min of carboetomidate exposure. At the end of each study, tadpoles were returned to fresh water to ensure reversibility of hypnotic action. No evidence of toxicity was observed; all anesthetized tadpoles recovered their righting reflexes when returned to fresh oxygenated water.

Figure 2A:
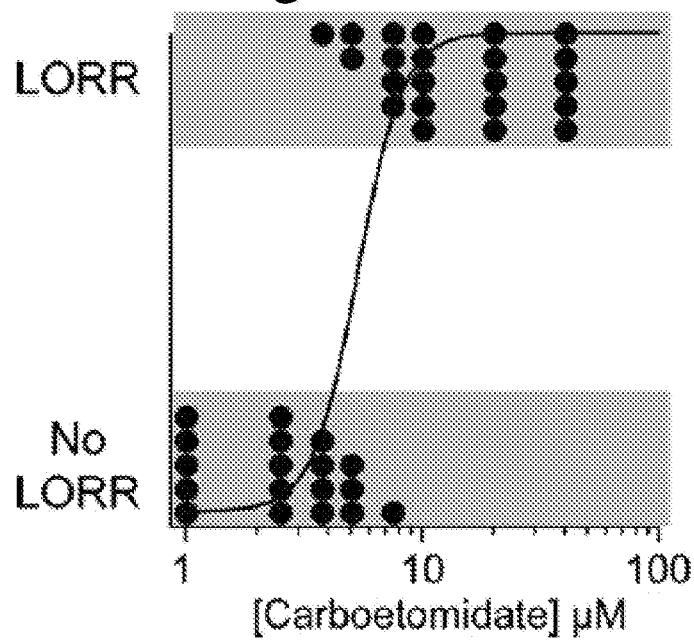
FIGS. 2A and 2B shows the carboetomidate concentration-response curve for loss of righting reflex (LORR) in tadpoles.
Figure 2B:
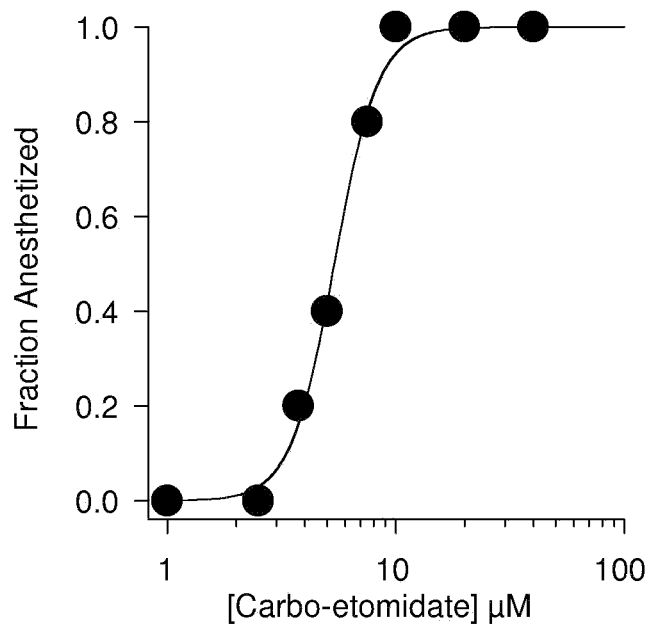

FIG. 2 shows the carboetomidate concentration-response curve for anesthesia. The fraction of tadpoles anesthetized in each group increased with carboetomidate concentration and at the highest carboetomidate concentrations (10-40 μM), all tadpoles were anesthetized. From this data, carboetomidate's anesthetic EC$_{50}$ (i.e. the concentration at which 50% of tadpoles were anesthetized) was determined to be 5.4±0.5 μM using the quantal method described in Waud, D. R., J Pharmacol Exp Ther (1972) 183(3): 577-607.

Example 3

Modulation by carboetomidate of Wild-type $\alpha_1\beta_2\gamma_{2L}$ and etomidate-insensitive $\alpha_1\beta_2$M286W$\gamma_{2L}$ GABA$_A$ Receptors Carboetomidate was designed to produce anesthesia by the same molecular mechanism as (R)-etomidate: by enhancing GABA$_A$ receptor function. Human GABA$_A$ receptors composed of $\alpha_1\beta_2\gamma_{2L}$ subunits were expressed in *Xenopus laevis* oocytes and used to study the effect of carboetomidate on GABA$_A$ receptor mediated currents using the two-microelectrode voltage clamp technique described in Raines et al., Anesth Analg (2003) 96(1): 112-8. This subunit combination was chosen because it forms the most prevalent GABA$_A$ receptor subtype in the brain and is known to be etomidate-sensitive.

Figure 3A:
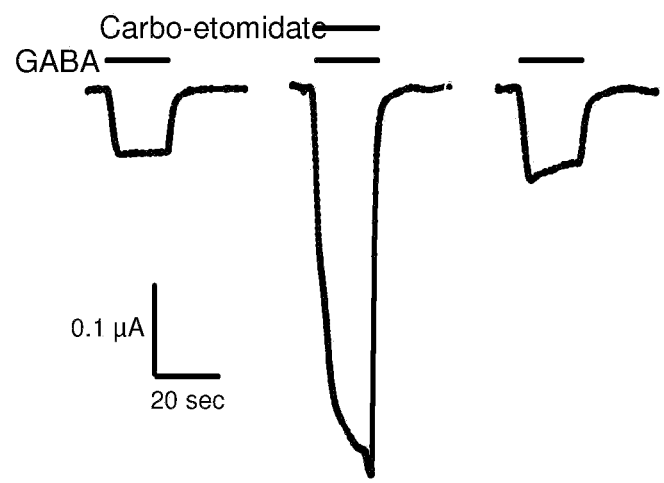
FIG. 3 shows electrophysiological traces demonstrating enhancement of currents mediated by human $\alpha_1\beta_2\gamma_{2L}$ $GABA_A$ receptors (FIG. 3A) and etomidate-insensitive mutant $\alpha_1\beta_2M286W\gamma_{2L}$ $GABA_A$ (FIG. 3B) expressed in Xenopus oocytes by 10 μM carboetomidate. These results indicate that carboetomidate binds to the same site on the $GABA_A$ receptor as etomidate. The first and last traces are controls (i.e., no anesthetic). The middle trace shows the enhancing effect of carboetomidate. All currents in FIG. 3A were evoked in the same cell; similarly all currents in FIG. 3B were also evoked in the same cell.

In each oocyte, a GABA concentration of 3 μM, which evokes ~10-20% of the maximal response evoked by 1 mM GABA (a receptor-saturating GABA concentration) in wild-type receptors was used. To assess the effect carboetomidate on GABAergic currents, the "control" current evoked by GABA alone was measured. After a 5 min recovery period, the "test" peak current was measured by exposing oocytes to both anesthetic and GABA. After another 5 min recovery period, the control experiment was repeated to assure reversibility. FIG. 3A shows representative control and test traces obtained in the absence and presence of anesthetic, respectively in the same oocyte. It was found that, at approximately twice its anesthetic EC50 (i.e. 10 μM), carboetomidate enhanced the amplitudes of GABA-evoked currents by 4-fold.

Figure 3B:
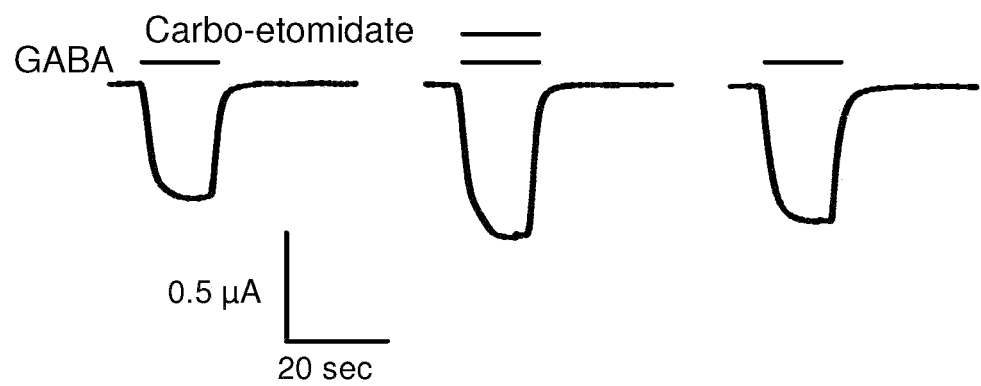

Mutant $\alpha_1\beta_2$M286W$\gamma_{2L}$ GABA$_A$ receptors were expressed in *Xenopus laevis* oocytes and used to study the effect of carboetomidate on mutant GABA$_A$ receptor mediated currents using the two-microelectrode voltage clamp technique. In each oocyte, a GABA concentration of 0.3 μM, which evokes ~10-20% of the maximal response evoked by 1 mM GABA (a receptor-saturating GABA concentration) in wild-type receptors was used. A lower GABA concentration was used because these mutant GABA$_A$ receptors are 10-fold more sensitive to GABA than wild-type receptors used in Example 2. FIG. 3B shows representative control and test traces obtained in the absence and presence of anesthetic, respectively in the same oocyte. It was found that, at approximately twice its anesthetic EC50 (i.e. 10 μM), carboetomidate had little effect on the amplitude of GABA-evoked currents. As this etomidate binding site mutation attenates GABA$_A$ receptor sensitivity to both etomidate and carboetomidate, it can be concluded that both etomidate and carboetomidate likely bind to the same site on the GABA$_A$ receptor.

Figure 4:
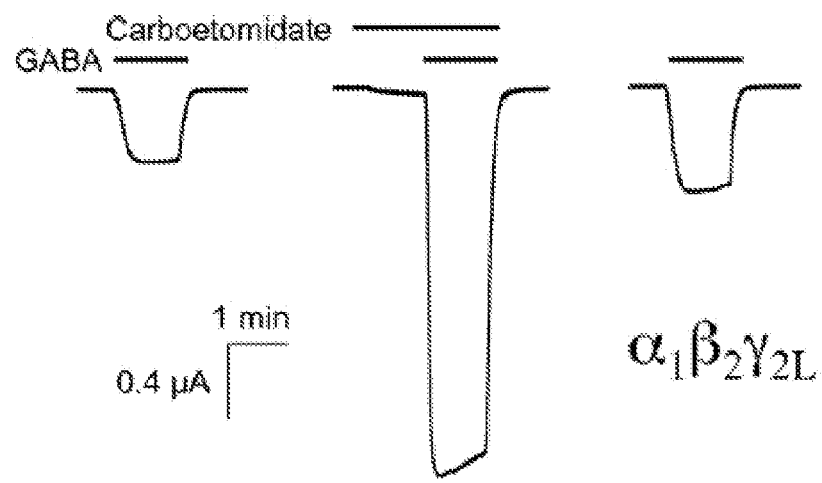
FIG. 4 shows a further example of carboetomidate modulation of human γ-aminobutyric acid (GABA) type A receptor function.
Figure 4:
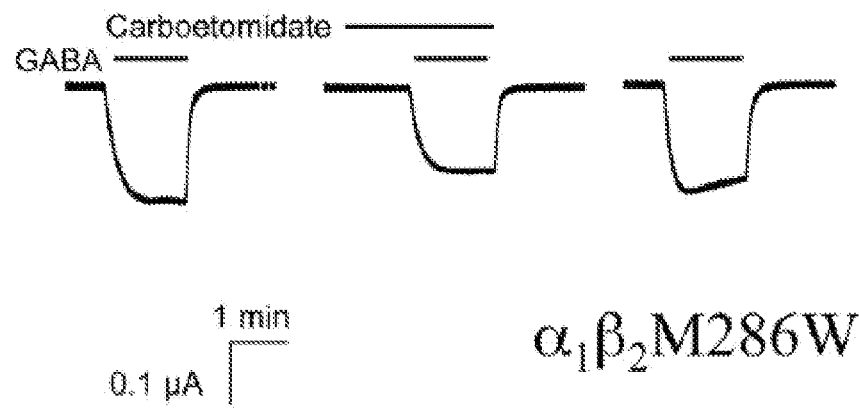

Further representative electrophysiologic traces elicited by EC$_{5-10}$ GABA in the absence or presence of 10 μM carboetomidate are shown in FIG. 4A (wild-type $\alpha_1\beta_2\gamma_{2L}$ GABA$_A$ receptors) and FIG. 4B (etomidate-insensitive mutant $\alpha_1\beta_2$M286W$\gamma_{2L}$ GABA$_A$ receptors). Carboetomidate significantly enhanced currents mediated by wild-type receptors (390±80%) but did not enhance currents mediated by etomidate-insensitive mutant receptors (−9±16%).

Example 4

Carboetomidate is Less Potent an Inhibitor of Cortisol Synthesis by Human Adrenocortical Cells than is Etomidate Next, the ability of carboetomidate to inhibit cortisol synthesis by human adrenocotical cells was examined. Human adrenocortical cell line H295R (NCI-H295R; ATCC #CRL-2128) was used as in vitro system to assess and compare inhibitory action of etomidate and carboetomidate on cortisol synthesis/H295R cells express most of the key enzymes necessary for steroidogenesis, including all of those required for cortisol biosynthesis (e.g., 11β-hydroxylase). When stimulated with foskolin, these cells produce cortisol and secrete it into the medium where it can be readily measured. Inhibition of 11β-hydroxylase blocks cortisol synthesis and reduces concentration of cortisol in the cell culture medium, forming the basis of the assay.

H295R cells were grown to near confluence in growth medium (DMEM/F12 supplemented with 1% ITS containing insulin, transferrin, selenium, and linoleic acid, 2.5% NuSerum and Pen/Sterp). The growth medium was then replaced with an assay medium that promotes cortisol synthesis (DMEM/F12 supplemented with 0.1% ITS and 20 µM forskolin) along with either etomidate or carboetomidate (or nothing for controls). After allowing 48 hrs for forskolin-stimulated cortisol synthesis, 1.2 ml of the assay medium was collected, centrifuged (to remove cells and debris), and the cortisol concentration in the supernatant measured by an Enzyme-Linked ImmunoSorbent Assay (ELISA).

Figure 5:
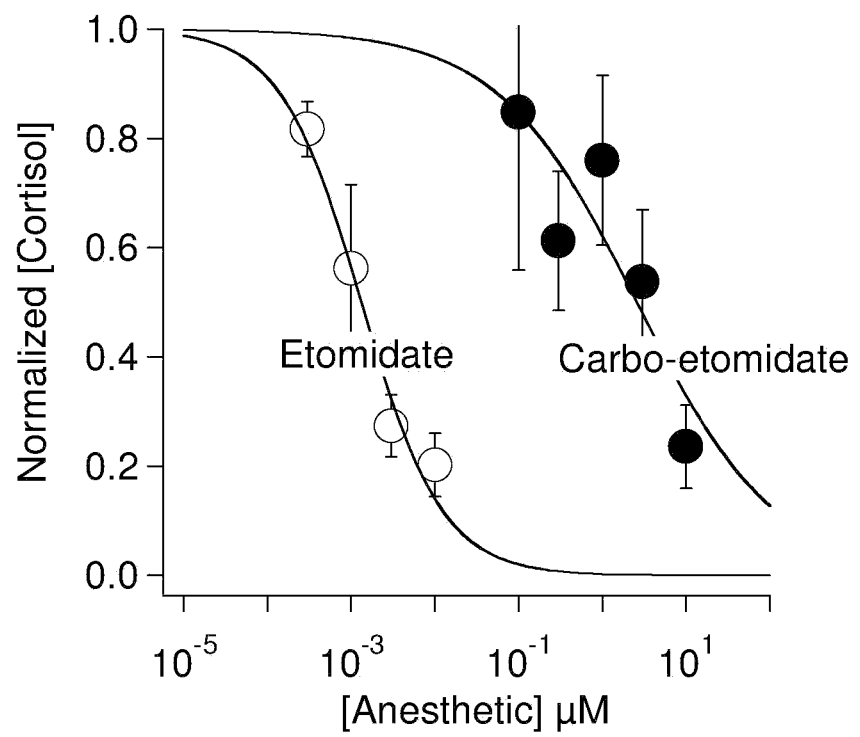
FIG. 5 is a graph showing the anesthetic concentration-response curves for inhibition of cortisol synthesis by H295R adrenocortical cells. Note that carboetomidate is at least three orders of magnitude less potent an inhibitor of cortisol production than etomidate.

FIG. 5 shows that both etomidate and carboetomidate reduced the concentration of cortisol in the assay medium in a concentration dependent manner. Although both hypnotics inhibited cortisol synthesis in a concentration-dependent manner, the concentration ranges over which this inhibition occurred differed by three orders of magnitude. For etomidate, the half-maximal inhibitory concentration (IC50) was 1.3±0.02 nM whereas that for carboetomidate was 2000-fold higher (2.6±1.5 µM).

Example 5

Carboetomidate is a Potent and Ultra-Short Acting General Anesthetic in Rats

Etomidate or carboetomidate was administered to Sprague Dawley rats as an IV bolus into their tail veins. A rat was judged to have LORR if it failed to right itself (onto all four paws) following drug administration. LORR was defined as the time from drug injection until the animal spontaneously righted itself. The $ED_{50}$ for LORR upon bolus anesthetic administration was determined from the anesthetic dose-dependence of LORR.

Figure 6:
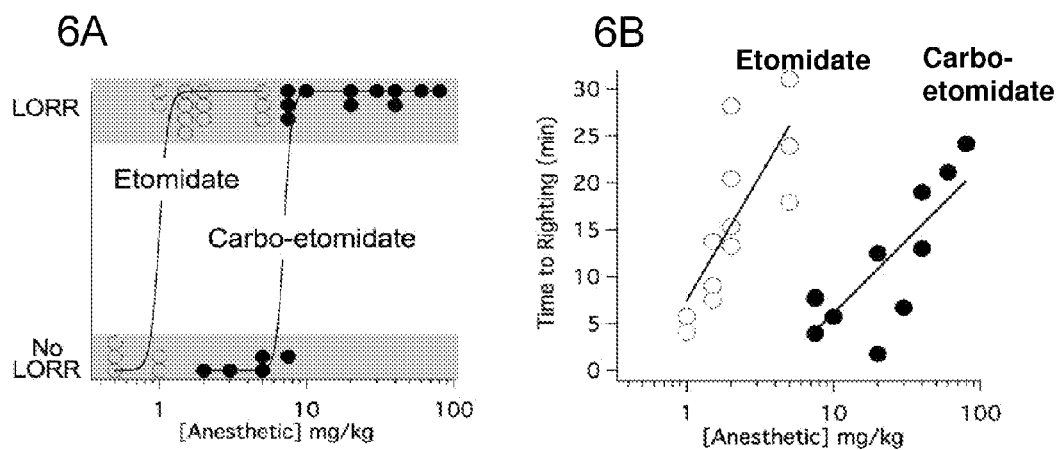
FIG. 6a is a graph showing anesthetic dose-response curves for LORR in rats following IV bolus administration. Each data point is from a single rat.
FIG. 6b is a graph showing the relationship between anesthetic dose and the time required for a rat to right itself following anesthetic administration. Each data point is from a single rat.

FIG. 6a shows the etomidate and carboetomidate dose-response relationships for LORR in rats. The fraction of rats that had LORR increased with anesthetic dose. At the highest doses, all rats were anesthetized and there was no obvious anesthetic toxicity. From these data, the $ED_{50}$s for LORR following bolus administration of etomidate and carboetomidate were determined to be 1.00±0.03 mg/kg (n=18) and 7±2 mg/kg (n=16), respectively. At doses sufficient to produce LORR in rats, both anesthetics produced LORR within several seconds of IV bolus administration.

The inventors discovered that the onset time for LORR with carboetomidate was slower than the time they had previously observed with etomidate, as described in Cotton et al., Anesthesiology, (2009) 111: 240-249. The inventors quantified this difference using equihypnotic doses of carboetomidate and etomidate (28 and 4 mg/kg, respectively; 4×$ED_{50}$ for LORR) (Cotton et al., Anesthesiology, (2009) 111: 240-249). The onset time for LORR with carboetomidate was 33±22 s (n=10; range 10-63 s) when compared with 4.5±0.6 s (n=4; range 4-5 s) with etomidate.

FIG. 6b shows that for both anesthetics duration of anesthesia (i.e. the time to spontaneous righting) increased approximately linearly with the logarithm of the anesthetic dose. The slope of this relationship was similar for etomidate (27±7) and carboetomidate (16±4). Because the slope of this relationship depends upon the anesthetic's half-life in the brain, these results suggest that etomidate and carboetomidate are cleared from the brain at similar rates.

Example 6

Carboetomidate has Superior Hemodynamic Stability

Etomidate is often chosen for anesthetic induction over other agents in the critically ill patient because it better preserves hemodynamic stability. To determine whether carboetomidate similarly preserves hemodynamic stability, we measured and compared the actions of propofol, etomidate, and carboetomidate on heart rate and blood pressure in rats. To compare these drugs at equianesthetic doses, each was administered intravenously at twice its $ED_{50}$ for LORR (i.e., 8 mg/kg propofol, 2 mg/kg etomidate, and 14 mg/kg carboetomidate). Following animal acclimatization, data were recorded for 5 min prior to (baseline) and for 15 min after anesthetic injection. The average mean blood pressure was calculated at each 30-second epoch during this study period.

Figure 7A:
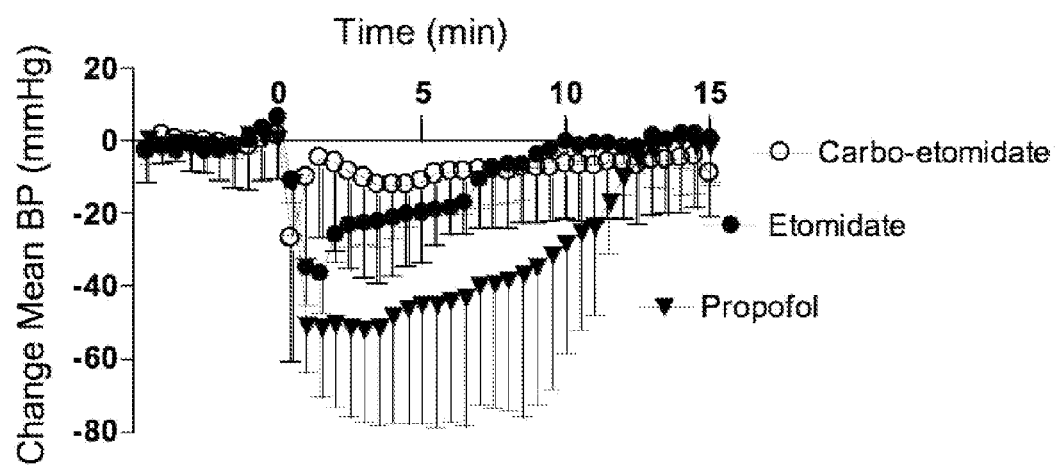
FIG. 7A shows a plot over time of mean blood pressure in rats following administration of equianesthetic doses of propofol, etomidate, and carboetomidate and demonstrates that carboetomidate depresses blood pressure significantly less than propofol or etomidate. Each point represents the mean during a 30 sec. epoch. The error bars are the standard deviations. All anesthetics were given at doses that are twice their ED50s for LORR. In propofol and etomidate groups, n=3 rats. In the carboetomidate group, n=4 rats.

FIG. 7A shows that rats in each group had similar mean heart rates and blood pressure at baseline over the first 5 minutes. While rats were anesthetized (i.e. the first 5-10 min after anesthetic administration), mean blood pressure decreased for all three anesthetics. However at nearly all time points during anesthesia, the magnitude of this decrease was less for carboetomidate and etomidate vs. propofol.

Figure 7B:
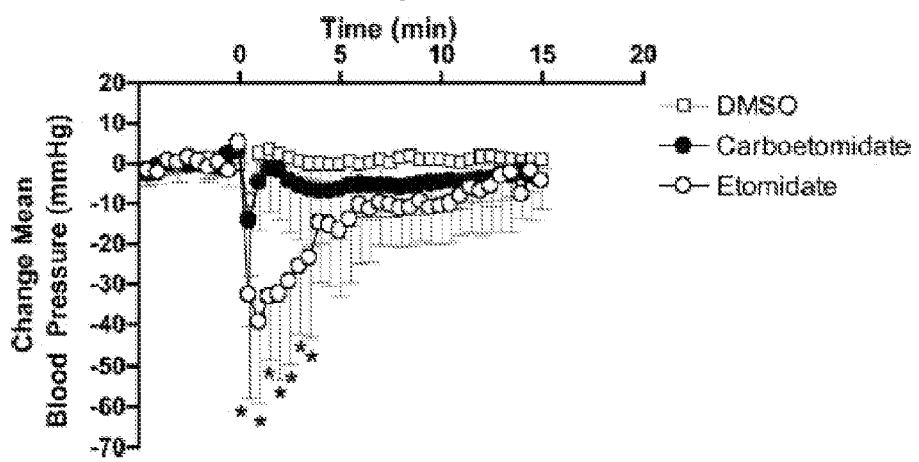
FIG. 7B shows the effects of 14 mg/kg of carboetomidate (n=7), 2 mg/kg of etomidate (n=6), and dimethyl sulfoxide (DMSO) vehicle alone (n=4) on mean blood pressure in rats. Hypnotics were given at doses equal to twice their respective $ED_{50}s$ for loss of righting reflex in DMSO vehicle. All rats received the same quantity of DMSO vehicle (350 µl/kg). Hypnotic in DMSO vehicle or DMSO vehicle alone was injected at time 0. Each data point represents the average (±SD) change in mean blood pressure during each 30-s epoch. * P<0.05 versus DMSO vehicle alone.

Similarly, FIG. 7B shows the effects of 14 mg/kg of carboetomidate (n=7), 2 mg/kg of etomidate (n=6), and DMSO vehicle (n=4) on mean arterial blood pressure in rats. For carboetomdiate and etomidate, these were equihypnotic doses. During the study period, the effect of carboetomidate on mean blood pressure was not significantly greater than that of DMSO vehicle alone (P>0.05 by two-way ANOVA). However, at times from 30 to 210 s after administration, etomidate significantly reduced mean blood pressure relative to vehicle. Baseline mean blood pressures for vehicle, carboetomidate, and etomidate groups were similar (P=0.15 by ANOVA) at 114±5, 116±9, and 127±17 mmHg, respectively.

Example 7

Unlike (R)-Etomidate, Carboetomidate Does Not Suppress Adrenocortical Function 15 min After Administration Male Sprague Dawley rats were pre-treated with dexamethasone to inhibit endogenous ACTH production and minimize baseline serum corticosterone concentrations. Into each rat, an IV bolus of DMSO vehicle (control), 2 mg/kg etomidate, or 14 mg/kg carboetomidate was given. For etomidate and carboetomidate these are equianesthetic bolus doses (i.e. 2×ED50 for LORR). Immediately thereafter, Cortrosyn (i.e. $ACTH_{1-24}$) was injected to stimulate steroid production. Fifteen minutes after $ACTH_{1-24}$ administration an ~0.3 ml blood sample was drawn to measure the $ACTH_{1-24}$-stimulated serum corticosterone concentration. Baseline serum corticosterone concentrations in rats (n=12) averaged 39±49 ng/ml and were not significantly different among the three groups (carboetomidate, etomidate, and control). Administration of $ACTH_{1-24}$ stimulated adrenocortical steroid production in all three groups.

Figure 8:
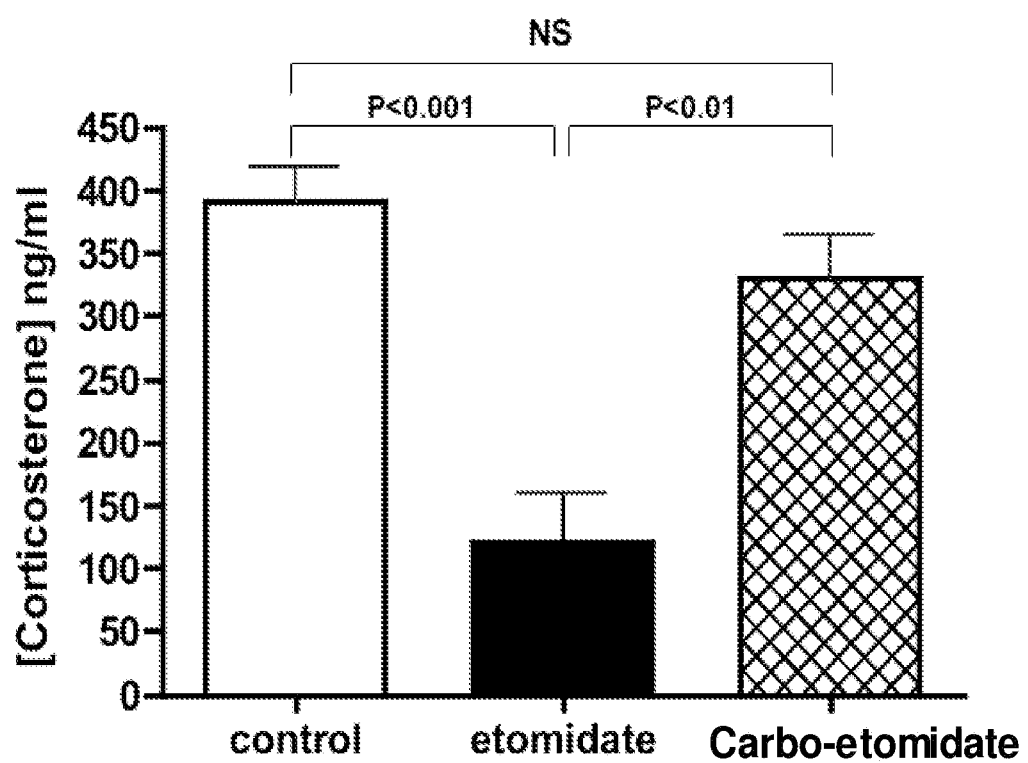
FIG. 8 shows that the serum concentration of corticosterone (an adrenocortical steroid) was relatively unchanged versus vehicle (control) 15 minutes after administration of carboetomidate whereas it was significantly reduced by an equianesthetic dose of etomidate. In these rats, corticosterone production was stimulated with $ACTH_{1-24}$ 15 minutes after anesthetic or vehicle administration and then serum corticosterone concentrations were measured 15 minutes later. Doses of etomidate and carboetomidate were 2× their respective ED50s for LORR. Four rats were used in each group. The error bars are the standard deviations.

FIG. 8 shows that injection of $ACTH_{1-24}$ stimulated adrenocortical steroid production as all rats had significantly higher serum corticosterone concentrations fifteen minutes after $ACTH_{1-24}$ administration. However rats that had received (R)-etomidate prior to $ACTH_{1-24}$ stimulation had significantly lower serum corticosterone concentrations (67% less) than those that had received either vehicle or an equianesthetic dose of carboetomidate. In contrast, rats that had received carboetomidate had serum corticosterone concentrations that were not different from those that had received only vehicle.

Discussion

Carboetomidate is a pyrrole analog of etomidate that retains the hypnotic action of etomidate, GABAA receptor modulatory activity, and hemodynamic stability. However, it is a three orders of magnitude less-potent inhibitor of adrenocortical cortisol synthesis than etomidate, and unlike etomidate, it does not suppress adrenocortical function in rats at hypnotic doses.

Etomidate suppresses adrenocortical function primarily by inhibiting 11β-hydroxylase (CYP11B1), a member of the cytochrome P450 superfamily of enzymes. 11β-Hydroxylase is required for the synthesis of cortisol, corticosterone, and aldosterone. This suppression occurs at very low etomidate concentrations, which is thought to reflect a very high affinity of etomidate to the active site of the enzyme. See for example, Zolle et al., J Med Chem (2008) 51:2244-2253 and Roumen et al., J Comput Aided Mol Des (2007) 21: 455-471, content of both of which is herein incorporate by reference. The inventors designed carboetomidate to inhibit and/or reduce the high affinity of etomidate to 11β-hydroxylase due to the basic nitrogen in its imidazole ring. Without wishing to be bound by theory, the basic nitrogen in the imidazole ring of the etomidate with the heme iron of the active site leading to high affinity of etomidate for 11β-hydroxylase. This interaction has been observed in the binding of other imidazole-containing drugs to various cytochrome P450 enzymes using crystallographic techniques. For example, the inhibitor 4-(4-chlorophenyl)imidazole binds to the active site of enzyme 2B4 in a single orientation with the basic nitrogen of its imidazole ring coordinated to the enzyme's heme iron at a bond distance of 2.14 Å (Scott et al., J Biol Chem (2004) 279: 27294-27301, content of which is herein incorporated by reference). This binding triggers a conformational transition in which the enzyme closes tightly around the bound ligand. Similarly, imidazole-containing anti-fungal agents bind within the active sites of CYP130 and CYP121 where they form a coordination bond between basic nitrogen and the heme iron of the enzyme. See for example, Ouelletet et al., J Biol Chem (2008) 283: 5069-5080 and Seward et al., J Biol Chem (2006) 281: 39437-39443, content of both of which is herein incorporated by reference. Evidence of such coordination has also been found using spectroscopic techniques, as the heme group serves as a chromophore that undergoes a characteristic spectral shift when a coordination bond is formed with an imidazole-containing inhibitor. See for example, Ouelletet et al., J Biol Chem (2008) 283: 5069-5080; Yano et al., J Med Chem (2006) 49: 6987-7001; Locuson et al., Drug Metab Dispos (2007), 35: 614-622; and Hutzler et al., Chem Res Toxicol (2006) 19: 1650-1659, content of all of which is herein incorporated by reference in its entirety. Although the interactions of etomidate with 11β-hydroxylase have not been defined experimentally using crystallographic or spectroscopic techniques, in silico homology modeling suggests that coordination between the basic nitrogen of hypnotic and the heme iron of enzyme also contributes to high-affinity binding (Roumen et al., J Comput Aided Mol Des (2007) 21: 455-471).

The inventors used an adrenocortical carcinoma cell assay to compare the inhibitory potencies of carboetomidate and etomidate. This assay has been used previously to compare the potencies with which drugs inhibit the synthesis of adrenocortical steroids. See for example Fallo et al., Endocr Res (1996) 22: 709-715; Fallo et al., Chemotherapy (1998) 44: 129-134; and Fassnacht et al., Eur J Clin Invest (2000) 30 (suppl 3): 76-82, content of all of which is herein incorporated by reference. The results showed that carboetomidate is a three orders of magnitude less-potent inhibitor of cortisol synthesis than etomidate. This is consistent with an important role of the basic nitrogen of hypnotic in stabilizing binding to the enzyme and provides strong evidence that high-affinity binding of etomidate to 11β-hydroxylase can be designed out of etomidate by replacing this nitrogen with other chemical groups (in this case, CH) that cannot coordinate with heme iron. As a consequence of its low adrenocortical inhibitory potency, carboetomidate failed to inhibit $ACTH_{1-24}$-stimulated production of corticosterone in rats when given as a bolus at a hypnotic dose.

Although carboetomidate is a three orders of magnitude less-potent inhibitor of in vitro cortisol synthesis than etomidate, it is only modestly less potent as a hypnotic. It has one-third and one-seventh the hypnotic potency of etomidate in tadpoles (Husain et al., J Med Chem (2003) 46: 1257-1265) and rats (Cotten et al., Anesthesiology (2009) 111: 240-240) respectively. These results show that one may alter anesthetic structure to dramatically reduce the potency for producing an undesirable side effect without greatly impacting hypnotic potency.

In common with etomidate, carboetomidate significantly enhances the function of wild-type $\alpha_1\beta_2\gamma_{2L}$, $GABA_A$ receptors. For a description of direct activation and agonist modulation of $GABA_A$ receptors see Rusch et al., J Biol Chem (2004) 279: 20982-20992, content of which is herein incorporated by reference in its entirety. Without wishing to be bound by a theory, carboetomidate also produces hypnosis via actions on the $GABA_A$ receptor. Previous electrophysiologic studies of the $GABA_A$ receptor have shown that a mutation in the β subunit at the putative etomidate binding site (M286W) nearly completely abolishes etomidate enhancement (Siegwart et al., J Neurochem (2002) 80: 140-148, content of which is herein incorporated by reference in its entirety). The results presented herein show that this mutation also abolishes enhancement by carboetomidate, demonstrating that carboetomidate can modulate $GABA_A$ receptor function by binding to the same site on the $GABA_A$ receptor as etomidate.

The magnitude of potentiation that the inventors observed with 10 µM carboetomidate (390±80%) in the current study is no greater than that observed in inventors' previous study with 4 µM etomidate (660±240%). This may imply that carboetomidate is less potent and/or efficacious at the $GABA_A$ receptor than is etomidate. Without wishing to be bound by theory, this may explain why a higher concentration (in the tadpole assay) and dose (in the rat assay) of carboetomidate than etomidate was needed to produce LORR. It also indicates that the basic nitrogen in the imidazole ring of etomidate contributes modestly to etomidate's action on $GABA_A$ receptors.

The onset of LORR was slower with carboetomidate than with etomidate. The reason for this is unclear. However, as both hypnotics potentiate the $GABA_A$ receptor, it seems likely that onset is delayed because carboetomidate reaches its site of action in the brain more slowly than etomidate.

References

1. Hotchkiss, R. S. and I. E. Karl, The pathophysiology and treatment of sepsis. N Engl J Med, 2003. 348(2): p. 138-50.
2. Husain, S. S., et al., 2-(3-Methyl-3H-diaziren-3-yl)ethyl 1-(1-phenylethyl)-1H-imidazole-5-carboxylate: a derivative of the stereoselective general anesthetic etomidate for photolabeling ligand-gated ion channels. J Med Chem, 2003. 46(7): p. 1257-65.
3. Arden, J. R., F. O. Holley, and D. R. Stanski, Increased sensitivity to etomidate in the elderly: initial distribution versus altered brain response. Anesthesiology, 1986. 65(1): p. 19-27.
4. Jurd, R., et al., General anesthetic actions in vivo strongly attenuated by a point mutation in the GABA(A) receptor beta3 subunit. Faseb J, 2003. 17(2): p. 250-2.
5. Rusch, D., H. Zhong, and S. A. Forman, Gating allosterism at a single class of etomidate sites on alpha1beta2gamma2L GABA A receptors accounts for both direct activation and agonist modulation. J Biol Chem, 2004. 279(20): p. 20982-92.
6. Li, G. D., et al., Identification of a $GABA_A$ receptor anesthetic binding site at subunit interfaces by photolabeling with an etomidate analog. J Neurosci, 2006. 26(45): p. 11599-605.
7. Stewart, D., et al., Tryptophan mutations at azi-etomidate photo-incorporation sites on alpha1 or beta2 subunits enhance $GABA_A$ receptor gating and reduce etomidate modulation. Mol Pharmacol, 2008. 74(6): p. 1687-95.
8. Watt, I. and I. M. Ledingham, Mortality amongst multiple trauma patients admitted to an intensive therapy unit. Anaesthesia, 1984. 39(10): p. 973-81.
9. Ray, D. C. and D. W. McKeown, Effect of induction agent on vasopressor and steroid use, and outcome in patients with septic shock. Crit. Care, 2007. 11(3): p. R56.
10. Sprung, C. L., et al., Hydrocortisone therapy for patients with septic shock. N Engl J Med, 2008. 358(2): p. 111-24.
11. de Jong, F. H., et al., Etomidate suppresses adrenocortical function by inhibition of 11 beta-hydroxylation. J Clin Endocrinol Metab, 1984. 59(6): p. 1143-7.
12. Lamberts, S. W., et al., Differential effects of the imidazole derivatives etomidate, ketoconazole and miconazole and of metyrapone on the secretion of cortisol and its precursors by human adrenocortical cells. J Pharmacol Exp Ther, 1987. 240(1): p. 259-64.
13. Roumen, L., et al., Construction of 3D models of the CYP11B family as a tool to predict ligand binding characteristics. J Comput Aided Mol Des, 2007. 21(8): p. 455-71.
14. Zhao, Y., et al., Structure of microsomal cytochrome P450 2B4 complexed with the antifungal drug bifonazole: insight into P450 conformational plasticity and membrane interaction. J Biol Chem, 2006. 281(9): p. 5973-81.
15. Podust, L. M., T. L. Poulos, and M. R. Waterman, Crystal structure of cytochrome P450 14alpha-sterol demethylase (CYP51) from *Mycobacterium tuberculosis* in complex with azole inhibitors. Proc Natl Acad Sci USA, 2001. 98(6): p. 3068-73.
16. Verras, A., A. Alian, and P. R. de Montellano, Cytochrome P450 active site plasticity: attenuation of imidazole binding in cytochrome P450(cam) by an L244A mutation. Protein Eng Des Sel, 2006. 19(11): p. 491-6.
17. Waud, D. R., On biological assays involving quantal responses. J Pharmacol Exp Ther, 1972. 183(3): p. 577-607.
18. Raines, D. E., R. J. Claycomb, and S. A. Forman, Modulation of GABA(A) receptor function by nonhalogenated alkane anesthetics: the effects on agonist enhancement, direct activation, and inhibition. Anesth Analg, 2003. 96(1): p. 112-8, table of contents.
19. Gooding J M, Weng J T, Smith R A, Berninger G T, Kirby R R: Cardiovascular and pulmonary responses following etomidate induction of anesthesia in patients with demonstrated cardiac disease. Anesth Analg 1979, 58:40-1.
20. Criado A, Maseda J, Navarro E, Escarpa A, Avello F: Induction of anaesthesia with etomidate: Haemodynamic study of 36 patients. Br J Anaesth 1980, 52:803-6.
21. Ebert T J, Muzi M, Berens R, Goff D, Kampine J P: Sympathetic responses to induction of anesthesia in humans with propofol or etomidate. Anesthesiology 1992, 76:725-33.
22. Sarkar M, Laussen P C, Zurakowski D, Shukla A, Kussman B, Odegard K C: Hemodynamic responses to etomidate on induction of anesthesia in pediatric patients. Anesth Analg 2005, 101:645-50.
23. Fragen R J, Shanks C A, Molteni A, Avram M J: Effects of Cotten et al. Carboetomidate: A Pyrrole Etomidate Analog etomidate on hormonal responses to surgical stress. Anesthesiology 1984, 61:652-6.
24. Ayub M, Levell M J: Inhibition of human adrenal steroidogenic enzymes in vitro by imidazole drugs including ketoconazole. J Steroid Biochem 1989, 32:515-24.
25. Wagner R L, White P F, Kan P B, Rosenthal M H, Feldman D: Inhibition of adrenal steroidogenesis by the anesthetic etomidate. N Engl J Med 1984, 310:1415-21.
26. Absalom A, Pledger D, Kong A: Adrenocortical function in critically ill patients 24 h after a single dose of etomidate. Anaesthesia 1999, 54:861-7.
27. Vinclair M, Broux C, Faure P, Brun J, Genty C, Jacquot C, Chabre O, Payen J F: Duration of adrenal inhibition following a single dose of etomidate in critically ill patients. Intensive Care Med 2007, 34:714-9.
28. Zolle I M, Berger M L, Hammerschmidt F, Hahner S, Schirbel A, Peric-Simov B: New selective inhibitors of steroid 11beta-hydroxylation in the adrenal cortex. Synthesis and structure-activity relationship of potent etomidate analogues. J Med Chem 2008, 51:2244-53.
29. Allolio B, Schulte H M, Kaulen D, Reincke M, Jaursch-Hancke C, Winkelmann W: Nonhypnotic low-dose etomidate for rapid correction of hypercortisolaemia in Cushing's syndrome. Klin Wochenschr 1988, 66:361-4.
30. Diago M C, Amado J A, Otero M, Lopez-Cordovilla J J: Anti-adrenal action of a subanaesthetic dose of etomidate. Anaesthesia 1988, 43:644-5.
31. Ledingham I M, Watt I: Influence of sedation on mortality in critically ill multiple trauma patients. Lancet 1983, 1:1270.
32. Bloomfield R, Noble D W: Etomidate and fatal outcome—even a single bolus dose may be detrimental for some patients. Br J Anaesth 2006, 97:116-7.
33. Jackson W L Jr: Should we use etomidate as an induction agent for endotracheal intubation in patients with septic shock?: A critical appraisal. Chest 2005, 127:1031-8.
34. Annane D: ICU physicians should abandon the use of etomidate! Intensive Care Med 2005, 31:325-6.
35. Hildreth A N, Mejia V A, Maxwell R A, Smith P W, Dart B W, Barker D E: Adrenal suppression following a single dose of etomidate for rapid sequence induction: A prospective randomized study. J Trauma 2008, 65:573-9.

36. Cuthbertson B H, Sprung C L, Annane D, Chevret S, Garfield M, Goodman S, Laterre P F, Vincent J L, Freivogel K, Rein-hart K, Singer M, Payen D, Weiss Y G: The effects of etomidate on adrenal responsiveness and mortality in patients with septic shock. Intensive Care Med 2009, 35: 1868-76.

37. Cotten J F, Husain S S, Forman S A, Miller K W, Kelly E W, Nguyen H H, Raines D E: Methoxycarbonyl-etomidate: A novel rapidly metabolized and ultra-short-acting etomidate analogue that does not produce prolonged adrenocortical suppression. Anesthesiology, 2009, 111:240-9.

38. Scott E E, White M A, He Y A, Johnson E F, Stout C D, Halpert J R: Structure of mammalian cytochrome P450 2B4 complexed with 4-(4-chlorophenyl)imidazole at 1.9-A resolution: Insight into the range of P450 conformations and the coordination of redox partner binding. J Biol Chem 2004, 279:27294-301.

39. Ouellet H, Podust L M, de Montellano P R: *Mycobacterium tuberculosis* CYP130: Crystal structure, biophysical characterization, and interactions with antifungal azole drugs. J Biol Chem 2008, 283:5069-80.

40. Seward H E, Roujeinikova A, McLean K J, Munro A W, Leys D: Crystal structure of the *Mycobacterium tuberculosis* P450 CYP121-fluconazole complex reveals new azole drug-P450 binding mode. J Biol Chem 2006, 281: 39437-43.

41. Yano J K, Denton T T, Cerny M A, Zhang X, Johnson E F, Cashman J R: Synthetic inhibitors of cytochrome P-450 2A6: Inhibitory activity, difference spectra, mechanism of inhibition, and protein cocrystallization. J Med Chem 2006, 49:6987-7001.

42. Locuson C W, Hutzler J M, Tracy T S: Visible spectra of type II cytochrome P450-drug complexes: Evidence that "incomplete" heme coordination is common. Drug Metab Dispos 2007, 35:614-22.

43. Hutzler J M, Melton R J, Rumsey J M, Schnute M E, Locuson C W, Wienkers L C: Inhibition of cytochrome P450 3A4 by a pyrimidineimidazole: Evidence for complex heme interactions. Chem Res Toxicol 2006, 19:1650-9.

44. Fallo F, Pilon C, Barzon L, Pistorello M, Pagotto U, Altavilla G, Boscaro M, Sonino N: Effects of taxol on the human NCI-H295 adrenocortical carcinoma cell line. Endocr Res 1996, 22:709-15.

45. Fallo F, Pilon C, Barzon L, Pistorello M, Pagotto U, Altavilla G, Boscaro M, Sonino N: Paclitaxel is an effective antiproliferative agent on the human NCI-H295 adrenocortical carcinoma cell line. Chemotherapy 1998, 44:129-34.

46. Fassnacht M, Hahner S, Beuschlein F, Klink A, Reincke M, Allolio B: New mechanisms of adrenostatic compounds in a human adrenocortical cancer cell line. Eur J Clin Invest 2000, 30(suppl 3):76-82.

47. Siegwart R, Jurd R, Rudolph U: Molecular determinants for the action of general anesthetics at recombinant alpha (2)beta(3)gamma(2)gamma-aminobutyric acid(A) receptors. J Neurochem 2002, 80:140-8.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

What is claimed:

1. A compound according to formula (I)

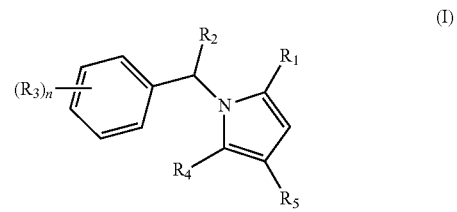

wherein:

(i)

$R_1$ is $L_1C(O)OT$;

$R_2$ is $C_1$-$C_{10}$ alkyl;

n is an integer from 0-5;

each $R_3$ is independently halogen or $R_2$;

$R_4$ and $R_5$ are independently H, halogen, CN or $CF_3$;

$L_1$ is a bond, or a $C_1$-$C_{10}$ alkylene;

$L_2$ is a bond, or $C_1$-$C_{10}$ alkylene;

T is ethyl, propyl, isopropyl, cyclopropyl, n-butyl, neopentyl, n-hexyl, cyclohexyl, n-octyl, n-decyl, n-dodecyl, n-hexadecyl, $CH_2CH(OH)CH_3$, $C_2$-$C_{10}$alkenyl, $C_2$-$C_{10}$alkynyl, nitrophenol, or cyclopropyl, wherein the backbone of the ethyl, propyl, isopropyl, n-butyl, neopentyl, n-hexyl, cyclohexy, n-octyl, n-decyl, or n-hexadecyl may contain one or more hetoeratoms; and pharmaceutically acceptable salts, stereoisomer mixtures, and enantiomers thereof; or (ii)

$R_1$ is $L_1C(O)OL_2C(O)OT$;

$R_2$ is $C_1$-$C_{10}$ alkyl;

n is an integer from 0-5;

each $R_3$ is independently halogen or $R_2$;

$R_4$ and $R_5$ are independently H, halogen, CN or $CF_3$;

$L_1$ is a bond, or a $C_1$-$C_{10}$ alkylene;

$L_2$ is a bond, or a $C_1$-$C_{10}$ alkylene;

T is H, a $C_1$-$C_{10}$ alkyl, $C_1$-$C_{10}$ alkyl substituted with an electron withdrawing group, $C_2$-$C_{10}$ alkenyl, $C_2$-$C_{10}$ alkenyl substituted with an electron withdrawing group, $C_2$-$C_{10}$ alkynyl, $C_2$-$C_{10}$ alkynyl substituted with an electron withdrawing group, nitrophenol, or cyclopropyl, wherein the backbone of the alkyl may contain one or more heteroatom; and pharmaceutically acceptable salts, stereoisomer mixtures, and enantiomers thereof.

2. The compound of claim 1, wherein said compound is present in the form of a pure enantiomer.

3. The compound of claim 2, wherein said enantiomer is the R enantiomer.

4. The compound of claim 1, wherein $R_1$ is $L_1C(O)OT$ and T is selected from the group consisting of $CH_2CH_3$, $CH_2CH(OH)CH_3$, and $CH_2CH_2CH_3$.

5. The compound of claim 1, wherein $R_1$ is $L_1C(O)OL_2C(O)OT$ and T is selected from the group consisting of H, $CH_3$, $CH_2CH_3$, $CH_2CH(OH)CH_3$, and $CH_2CH_2CH_3$.

6. The compound of claim 1, wherein $R_2$ is selected from the group consisting of $CH_3$, $CH_2CH_3$ and $CH_2CH_2CH_3$.

7. The compound of claim 1, wherein n is 0 or 1.

8. The compound of claim 1, wherein: (i) $R_1$ is $L_1CO_2L_2CO_2T$, $R_2$ is $CH_3$, n is 0, $L_1$ is a bond, and T is H, $CH_3$, $CH_2CH_3$, or $CH_2CH(OH)CH_3$; or (ii) $R_1$ is $L_1CO_2T$, $R_2$ is $CH_3$, n is 0, and T is $CH_2CH_3$, or $CH_2CH(OH)CH_3$.

9. The compound of claim 1, wherein both $R_4$ and $R_5$ are H.

10. The compound of claim 1, wherein at least one of $R_4$ and $R_5$ is H and the other is Br or CN.

11. The compound of claim 10, wherein $R_4$ is H and $R_5$ is Br or CN.

12. The compound of claim 10, wherein $R_4$ is Br or CN and $R_5$ is H.

13. The compound of claim 1, wherein the compound of formula (I) is selected from the group consisting of

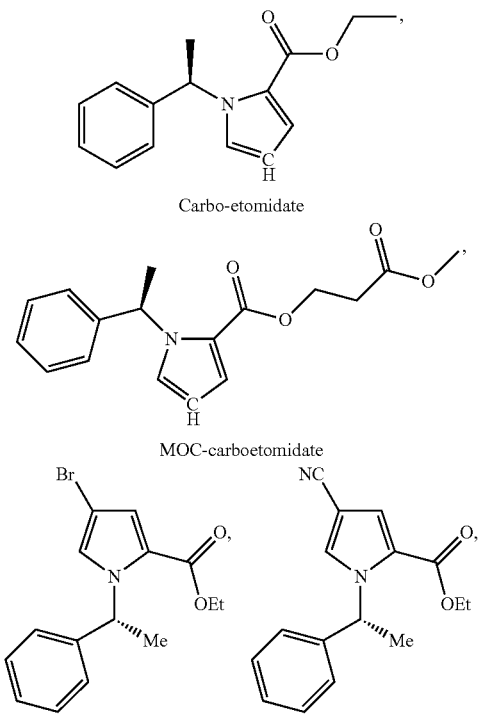

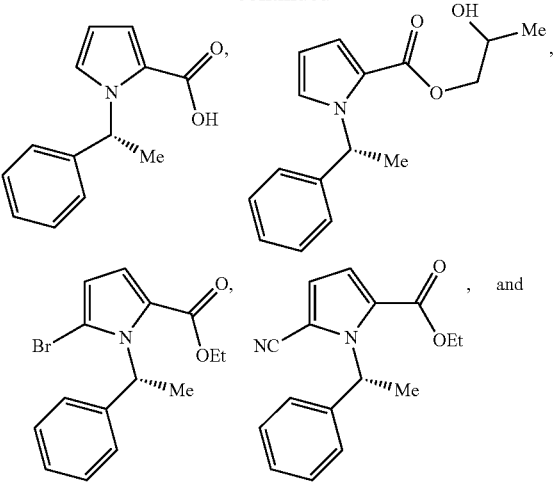

pharmaceutically acceptable salts, stereoisomer mixtures, and enantiomers thereof.

14. A pharmaceutical composition comprising a pharmaceutically effective amount of a compound of claim 1 and a pharmaceutically acceptable carrier.

15. A method for providing anesthesia to a subject comprising administering to said subject a pharmaceutical composition according to claim 14.

16. The compound of claim 1, wherein $L_1$ is a bond.

* * * * *

UNITED STATES PATENT AND TRADEMARK OFFICE
CERTIFICATE OF CORRECTION

PATENT NO. : 8,765,973 B2  
APPLICATION NO. : 13/382544  
DATED : July 1, 2014  
INVENTOR(S) : Douglas E. Raines et al.

It is certified that error appears in the above-identified patent and that said Letters Patent is hereby corrected as shown below:

In the Claims

Claim 13 (column 34, lines 1-10) recites the following chemical structure, which should be deleted.

"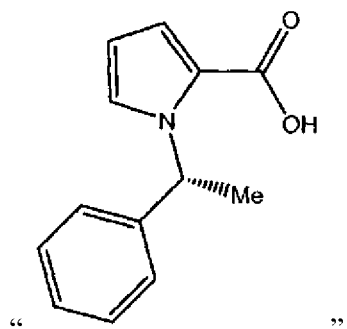"

Signed and Sealed this  
Fourteenth Day of July, 2015

Michelle K. Lee  
*Director of the United States Patent and Trademark Office*